US009164092B2

(12) United States Patent
Grove

(10) Patent No.: US 9,164,092 B2
(45) Date of Patent: Oct. 20, 2015

(54) DETECTION OF INTRAAMNIOTIC INFECTION

(71) Applicant: Hologic, Inc., Marlborough, MA (US)

(72) Inventor: Thomas H. Grove, Manhattan Beach, CA (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 14/175,476

(22) Filed: Feb. 7, 2014

(65) Prior Publication Data

US 2014/0154714 A1    Jun. 5, 2014

Related U.S. Application Data

(62) Division of application No. 12/952,017, filed on Nov. 22, 2010, now Pat. No. 8,663,576.

(60) Provisional application No. 61/264,633, filed on Nov. 25, 2009, provisional application No. 61/362,192, filed on Jul. 7, 2010.

(51) Int. Cl.
G01N 31/00 (2006.01)
G01N 33/53 (2006.01)
G01N 33/569 (2006.01)
G01N 33/68 (2006.01)

(52) U.S. Cl.
CPC ........ *G01N 33/56933* (2013.01); *G01N 33/689* (2013.01); *G01N 2800/36* (2013.01)

(58) Field of Classification Search
CPC ............ G01N 2800/36; G01N 33/689; G01N 33/56933
USPC ............ 435/7.1, 7.21; 436/501, 518; 424/9.1, 424/520; 422/430; 530/300, 350
See application file for complete search history.

(56) References Cited

U.S. PATENT DOCUMENTS

| | | | |
|---|---|---|---|
| 4,094,647 A | 6/1978 | Deutsch et al. | |
| 4,168,146 A | 9/1979 | Grubb et al. | |
| 4,235,601 A | 11/1980 | Deutsch et al. | |
| 4,361,537 A | 11/1982 | Deutsch et al. | |
| 4,703,017 A | 10/1987 | Campbell et al. | |
| 4,775,636 A | 10/1988 | Moeremans et al. | |
| 4,855,240 A | 8/1989 | Rosenstein et al. | |
| 4,857,453 A | 8/1989 | Ullman et al. | |
| 4,861,711 A | 8/1989 | Friesen et al. | |
| 4,943,522 A | 7/1990 | Eisinger et al. | |
| 6,008,056 A | 12/1999 | Thieme | |
| 6,283,761 B1 | 9/2001 | Joao | |
| 6,406,921 B1 | 6/2002 | Wagner et al. | |
| 8,663,576 B2 * | 3/2014 | Grove | 422/430 |
| 2007/0161125 A1 | 7/2007 | Rosenfeld et al. | |
| 2007/0178605 A1 | 8/2007 | Mor et al. | |

FOREIGN PATENT DOCUMENTS

| | | |
|---|---|---|
| WO | WO 2004/072638 | 8/2004 |
| WO | WO 2004/088324 | 10/2004 |
| WO | WO 2007/124439 | 11/2007 |
| WO | WO 2008/057160 | 5/2008 |
| WO | WO 2008/063928 | 5/2008 |

OTHER PUBLICATIONS

Bejar et al. "Antenatal origin of neurologic damage in newborn infants", Am. J. Obstet. Gynecol. 159: 357-362, 1988.
Gibbs et al. "Management of acute chorioamnionitis", Am. J. Obstet. Gynecol. 136: 709-713, 1980.
Gravett et al. "An experimental model for intraamniotic infection and preterm labor in rhesus monkeys", Am. J. Obstet. Gynecol. 171: 1660-1667, 1994.
Gravett, et al. "Proteomic analysis of cervical-vaginal fluid: Identification of novel biomarkers for detection of intra-amniotic infection", Journal of Proteome Research 6: 89-96, 2007.
Hitti et al. "Non-invasive diagnosis of intra-amniotic infection and preterm birth from proteomic analysis of vaginal fluid", Am. J. Obstet. Gynecol., pp. S5 (abstract), 2006.
Holst et al. "Interleukin-6 and interleukin-8 in cervical fluid in a population of Swedish women in preterm labor: relationship to microbial invasion of the amniotic fluid, intra-amniotic inflammation, and preterm delivery", Acta Obstet. Gynecol. Scand. 84: 551-557, 2005.
Jacobsson et al. "Monocyte chemotactic protein-1 in cervical and amniotic fluid: Relationship to microbial invasion of the amniotic cavity, intra-amniotic inflammation, and preterm delivery", Am. J. Obstet. Gynecol. 189: 1161-1167, 2003.
Morales, W. "The effect of chorioamnionitis on the development outcome of preterm infants at one year", Obstrt. Gynecol. 70: 183-186, 1987.
Newton, E.D. "Chorioanionitis and intraamniotic infection", Clinical Obstetrics and Gynecology 36(4): 795-808, 1993.
Ohlsson et al. "An analysis of antenatal tests to detect infection in preterm premature rupture of the membrane", Am. J. Obstet. Gynecol. 162: 809-818, 1990.
RayBiotech, Human Cytokine Array, Q7000 kit insert (pp. 1-3, Copyright 2007).
Romero et al. "The role of systemic and intrauterine infection in preterm parturition", Annals New York Academy of Sci. 622: 355-375, 1991.
Romero et al. "The diagnostic and prognostic value of amniotic fluid white blood cell count, glucose, interleukin-6, and Gram stain in patients with preterm labor and intact membranes", Am. J. Obstet. Gynecol. 169: 805-816, 1993.
Romero et al. "V. Prevalence, microbiology, and clinical significance of intraamniotic infection in women with preterm labor and intact membranes", Am. J. Obstet. Gynecol., 161: 817-824, 1989.
Watts et al. "The association of occult amniotic fluid infection with gestational age and neonatal outcome among women in preterm labor", Obstrt. Gynecol. 79: 351-357, 1992.
Ball et al. "An integrated approach utilizing artificial neural networks and SELDI mass spectometry for the classification of human tumors and rapid identification of potential biomarkers", Bioinformatics 18:395-404, 2002.
Bigelow et al. "Mucus observations in the fertile window: a better predictor of conception than timing of intercourse", Human Reproduction 19(4):889-892, 2004.

(Continued)

*Primary Examiner* — Lisa Cook
(74) *Attorney, Agent, or Firm* — Christopher De Vry; Arnold & Porter LLP

(57) ABSTRACT

The present invention concerns the identification of biomarkers and groups or combinations of biomarkers that can be used for non-invasive diagnosis of intra-amniotic infection, and diagnostic assays using such biomarkers.

24 Claims, 17 Drawing Sheets

(56) References Cited

OTHER PUBLICATIONS

Chernusevich et al. "An introduction to quadrupole-time-of-flight mass spectrometry", J. Mass Spectrometry 36:849-865, 2001.

Creasy and Resnik "Preterm labor and delivery", Maternal-Fetal Medicine, 4th Edition, Chapter 32: 498-531, 1999.

DiGiulio et al. "Microbial prevalence, diversity and abundance in amniotic fluid during preterm labor: a molecular and culture-based investigation", PLoS ONE 3(8): e3056:1-10, 2008.

Duff et al. "The course of labor in term pregnancies with chorioamnionitis", American Journal of Obstetrics and Gynecology 147:391-395,1983.

Eschenbach et al. "Prevalence of hydrogen peroxide-producing *lactobacillus* species in normal women and women with bacterial vaginosis", Journal Clinical Microbiology 27(2):251-256, 1989.

Gilstrap et al. "Intrapartum treatment of acute chorioamnionitis: impact on neonatal sepsis", Am. J. Obstetrics and Gynecology 159(3):579-583, 1988.

Gravett et al. "Independent associations of bacterial vaginosis and chlamydia trachomatis infection with adverse pregnancy outcome", JAMA 256(14):1899-1903, 1986.

Gravett et al. "Diagnosis of intra-amniotic infection by proteomic profiling and identification of novel biomarkers", JAMA 292(4):462-469, 2004.

Grether et al."Maternal infection and cerebral palsy in infants of normal birth weight", JAMA 278(3):207-211, 1997.

Haggerty et al. "Bacterial vaginosis and anaerobic bacteria are associated with endometritis", Clinical Infectious Diseases 39:990-995, 2004.

Han et al. "Uncultivated bacteria as etiologic agents of intra-amniotic inflammation leading to preterm birth", J. Clinical Microbiology 47:38-47, 2009.

Helmig et al. "Neutrophil elastase and secretory leukocyte protease inhibitor in prelabor rupture of membranes, parturition and intra-amniotic infection", J Maternal Fetal Neonatal Medicine 12(4):237-246, 2002.

Hillier et al. "The relationship of amniotic fluid cytokines and preterm delivery, amniotic fluid infection, histologic chorioamnionitis, and chorioamnion infection", Obstetrics Gynecology 81:941-948, 1993.

Issaq et al. "Breakthroughs and views: The SELDI-TOF MS approach t proteomics: protein profiling and biomarker identification ", Biochemical Biophysical Research Communication 292(3):587-592, 2002.

John et al. "Cervicovaginal secretions contribute to innate resistance to herpes simplex virus infection", Journal Infectious Diseases 192(10):1731-1740, 2005.

Khosravi et al. "An ultrasensitive immunoassay for prostate-specific antigen based on conventional colorimetric detection", Clinical Biochemistry 28:407-414,1995.

Kohler and Milstein "Continuous cultures of fused cells secreting antibody of predefined specificity", Nature 256:495-497,1975.

Li et al. "Proteomics and bioinformatics approaches for identification of serum biomarkers to detect breast cancer", Clinical Chemistry 48(8):1296-1304, 2002.

Lopez-Zeno et al. "A controlled trial of a program for the active management of labor", New England Journal of Medicine 326(7):450-454, 1992.

Maher et al. "HIV binding, penetration, and primary infection in human cervicovaginal tissue", Proc. Natl. Acad. Sci. USA 102 (32):11504-11509, 2005.

Mattsby-Baltzer et al. "IL-1beta, IL-6, TNFα, fetal fibronectin, and endotoxin in the lower genital tract of pregnant women with bacterial vaginosis", Acta Obstet. Gynecol. Scand 77(7):701-706, 1998.

Mikamo et al. "Intravaginal bacterial flora in patients with uterine cervical cancer. High incidence of detection of gardnerella vaginalis", J Infectious Chemotherapy 5(2):82-85, 1999.

Morris et al. "Bacterial vaginosis: a public health review", British Journal Obstetrics and Gynaecology 108(5):439-450, 2001.

Ness et al. "A cluster analysis of bacterial vaginosis-associated microflora and pelvic inflammatory disease", American Journal of Epidemiology162(6):585-590, 2005.

Newton et al. "Logistic regression analysis of risk factors for intra-amniotic infection", Obstetrics Gynecol. 73(4):571-575, 1989.

Ogino et al. "Establishment of a prediction method for premature rupture of membranes in term pregnancy using active ceruloplasmin in cervicovaginal secretion as a clinical marker", Journal Obstetrics Gynecology Research 31(5):421-426, 2005.

Petricoin et al. "Use of proteomic patterns in serum to identify ovarian cancer", Lancet 359:572-577, 2002.

Poli et al. "The effect of cytokines and pharmacologic agents on chronic HIV infection", AIDS Res Human Retroviruses 8(2):191-197, 1992.

Quinones-Mateu et al. "Human epithelial β-defensins 2 and 3 inhibit HIV-1 replication", Aids 17:F39-F48, 2003.

Schweitzer et al. "Measuring proteins on microarrays", Current Opinion Biotechnology 13(1):14-19, 2002.

Soper et al. "Risk factors for intraamniotic infection: a prospective epidemiologic study", American Journal of Obstetrics and Gynecology16:562-566, 1989.

Swamy et al. "Clinical utility of fetal fibronectin for predicting preterm birth", Journal Reproductive Medicine 50 (11):851-856, 2005.

Venkataraman et al. "Cationic polypeptides are required for anti-HIV-1 activity of human vaginal fluid", J Immunology 175(11):7560-7567, 2005.

Wilson and Nock "Protein microarray methods: recent developments in protein microarray technology", Angew. Chem. Int.. Ed. 42:494-500, 2003.

Zara et al. "Markers of local immunity in cervico-vaginal secretions of HIV infected women: implications for HIV shedding", Sex Transmittal Infections 80(2):108-112, 2004.

Zhou et al. "Solution and chip arrays in protein profiling", Trends Biotechnology 19:S34-S39, 2001.

Zhu et al. "Protein arrays and microarrays", Current Opinion Chemical Biology 5:40-45, 2001.

\* cited by examiner

DETECTION OF INTRAAMNIOTIC INFECTION

RELATED APPLICATIONS

This application is a divisional of, and claims the benefit under 35 U.S.C. §120 of, U.S. application Ser. No. 12/952,017, filed Nov. 22, 2010 now U.S. Pat. No. 8,663,576, which claims priority to, and the benefit under 35 U.S.C. §119(e) of, U.S. Provisional Application 61/264,633, filed Nov. 25, 2009, and U.S. Provisional Application 61/362,192, filed Jul. 7, 2010, the contents of each of which are hereby incorporated by reference in their entireties.

SEQUENCE LISTING

The content of the text file named "PTX-0014PR.txt" which was filed in the related application U.S. 61/264,633, was created on Nov. 24, 2009, and is 25,415 bytes in size, is hereby incorporated by reference in its entirety.

FIELD OF THE INVENTION

The present invention concerns tests for the diagnosis and/or assessment of the risk of intraamniotic infection (IAI) in pregnant women. The present invention further concerns tests, diagnostic algorithms, biomarkers, materials, methods, and devices relating to the use of biomarkers for the diagnosis of intra-amniotic infection in a pregnant female mammalian subject and providing diagnostic test systems for such diagnosis, and various other embodiments as described herein.

BACKGROUND OF THE INVENTION

Preterm birth is the leading cause of death in the first month of life and a contributing cause in more than a third of all infant deaths. Intra-amniotic infection (IAI) is one of the leading causes of idiopathic preterm birth <37 weeks of gestation. Other conditions associated with preterm birth include preterm labor, preterm rupture of membranes, preeclampsia, abrupta placenta, placenta previa, fetal growth retardation, excessive or inadequate amniotic fluid volume, fetal anomalies, intrauterine hemorrhage, diabetes, drug abuse and stress. Management of preterm labor and preterm birth may include treatment with tocolytic agents, and corticosteroids for fetal pulmonary maturation, if indicated. Narrow-spectrum antibiotics may be prescribed for Group B *Streptococcus* coverage pending negative culture results.

IAI is one of the most important causes of idiopathic preterm labor and preterm birth. IAI is a microbial invasion of the amniotic cavity and occurs in 10-15% of all preterm labor cases. (Newton E R. Clin Obstet Gynecol 1993; 36(4):795-808; Watts D H, et al., Obstet Gynecol 1992; 79:351-7; Romero R, et al., Am J Obstet Gynecol 1993; 169:805-16; Hillier S L, et al., Obstet Gynecol 1993; 81:941-8). Other terms used to describe IAI with or without intact membranes include: amniotic fluid infection, amnionitis, and clinical chorioamnionitis. In addition to the role of IAI as a cause of preterm labor, IAI is also associated with increased neonatal morbidity and mortality, particularly among preterm neonates. In general, a three to four-fold increase in perinatal mortality has been observed among low birth weight neonates born to mothers with IAI. There are also increases in respiratory distress syndrome, intraventricular hemorrhage, and neonatal sepsis. (Morales, W. J. Obstetrics and Gynecology 70:183, 1987). IAI has been independently implicated in neonatal periventricular leukomalacia and cerebral palsy; the risks of cerebral white matter damage and cerebral palsy are nine-fold greater in the setting of IAI. (Bejar, R., et al., Am. J. Obstet. Gynecol. 159:357, 1988; Grether, J. K. and Nelson, K. B. JAMA 278:207, 1997).

The majority of IAI cases, 80% to 90%, are subclinical (asymptomatic) other than preterm labor. Currently, the management of idiopathic preterm labor includes observation, treatment with tocolytic agents and possible confirmation of IAI by amniocentesis and culture. Amniotic fluid culture alone underestimates the true prevalence of IAI because of the presence of uncultivable microorganisms, difficulty in isolating fastidious microorganisms and previous antibiotic therapy (Romero, R. et al., Am. J. Obstet. Gynecol. 161:817, 1989). A positive IAI test or the present invention would provide a useful adjunct to the current diagnosis and treatment regimen available to the clinician. The accurate diagnosis of IAI is important for appropriate treatment of the mother with targeted antibiotics, withholding tocolytic therapy which is counterindicated in IAI as well as anticipating the location of delivery for the mother and the necessary level of care for the infant who may be very preterm and ill as an excess consequence of IAI.

A negative IAI test of the present invention provides reassurance that the etiology of preterm labor may be from sources other than infection. A negative test, in conjunction with 30 observation of other signs and/or symptoms, allows the physician to treat preterm labor.

Pathogenesis and Risk Factors:

Intra-amniotic infection likely occurs as a result of an ascending infection by lower genital tract microorganisms. The prevalence of IAI is strongly inversely associated with gestational age. (Watts D H, et al., Obstet Gynecol 1992; 79:351-7). Bacteria indigenous to the lower genital tract are recovered from the amniotic fluid of 10-20% of all women in preterm labor with intact amniotic membranes without clinical signs of IAI (Romero R, et al., Ann N Y Acad Sci 1991; 622:355-75) and in up to 67% of women in preterm labor with pregnancies ending at 23-24 weeks gestation. (Watts D H, et al., Obstet Gynecol 1992; 79:351-7). Moreover, these observations are supported by histologic chorioamnionitis which has been found in 60-90% of gestations ending between 20 and 24 weeks. These observations support the hypothesis that IAI is an important cause of idiopathic preterm labor, especially at early gestational ages.

Diagnosis:

An early diagnosis of IAI could allow timely treatment and intervention. However, there are multiple challenges in making the correct diagnosis. From the clinical perspective, early diagnosis is problematic because the clinical signs and symptoms of IAI occur late in the course of the infection, and are general and non-specific. The clinical criteria commonly used to diagnose IAI include preterm labor with maternal fever ($\geq 37.8°$ C.), along with two or more of the following: maternal leukocytosis ($\geq 15,000/mm^3$), maternal or fetal tachycardia, uterine tenderness, or foul-smelling amniotic fluid. (Gibbs R S, et al., Am J Obstet Gynecol 1980; 136(6):709-13). In a study by Watts, et al., of women with preterm labor, there was no difference in mean maximum maternal temperature, WBC count and differential between women with or without positive amniotic fluid cultures. Subclinical IAI is a term used to describe IAI and in which signs and symptoms are minimal or absent in approximately 88% cases with positive amniotic fluid cultures. (Watts D H, et al., Obstet Gynecol 1992; 79:351-7). The concept of subclinical IAI is further corroborated by the findings of Gravett, et al., utilizing a non-human primate model. These investigators demonstrated that following experimental IAI induced with Group B *strep-*

*tococcus*, fever and leukocytosis are present only 50% of the time at the onset of infection-induced preterm labor, which occurs 28 to 40 hours after experimental infection. (Gravett M G, et al., Am J Obstet Gynecol 1994; 171(6):1660-7).

Because of the inconsistency of clinical features, other adjunctive laboratory tests have 30 been utilized to aid in the diagnosis of IAI. These include: measurement of maternal C-reactive protein, direct examination of amniotic fluid for leukocytes or bacteria on Gram stain, amniotic fluid culture, measurement of amniotic fluid glucose concentrations, detection of amniotic fluid leukocyte esterase, detection of bacterial organic acids by gas-liquid chromatography, measurements of various amniotic fluid cytokines (e.g., interleukins 2, 4, 6, granulocyte colony-stimulating factor, and tumor necrosis factor-.alpha.), matrix metalloproteinase-9, lactoferrin, and assessment of fetal activity (biophysical profile) by ultrasonography. Measurement of cytokines or other biochemical factors is expensive, generally not clinically available, and is primarily a research tool. Further, the testing efficiency of these tests has not been consistently better than more readily available traditional tests such as amniotic fluid Gram stain and culture, amniotic fluid glucose concentrations, and detection of amniotic fluid leukocyte esterase. The efficiency of these tests has been previously extensively reviewed. (Ohlsson, A. and Wang, E.: An analysis of antenatal tests to detect infection at preterm rupture of the membranes. American Journal of Obstetrics and Gynecology 162:809, 1990). Although all have reasonable sensitivity, specificity, and predictive value, none are sufficiently sensitive or specific to be utilized independently of clinical features in the diagnosis of IAI.

Accordingly, there is a great need for new approaches that allow early and accurate diagnosis of IAI.

SUMMARY OF THE INVENTION

The present invention concerns tests for the diagnosis and/or assessment of the risk of intraamniotic infection (IAI) in pregnant women. The invention further concerns the identification and detection of biomarkers and groups or combinations of biomarkers that can be used for non-invasive diagnosis of intraamniotic infection (IAI), and diagnostic assays using such biomarkers, including a non-invasive test based on the use of a unique combination of three protein biomarkers to diagnose and/or assess the risk of intraamniotic infection (IAI) in pregnant women. The present invention relates generally to materials and processes used to create the intraamniotic infection laboratory developed test and in vitro diagnostic device and to biomarkers that have clinical utility in the diagnosis of IAI. In particular, the invention concerns materials and processes used to create an in vitro diagnostic device to diagnose or assess the risk of IAI by analyzing a biological sample, such as cervical vaginal fluid (CVF) obtained from a pregnant woman. Particularly, the present invention relates to biomarkers that, especially when used in combination with a diagnostic algorithm, have the ability to predict the presence of IAI using a non-invasive, cervical vaginal swab-based immunodiagnostic test with a high degree of accuracy. This unique combination of markers, when used in conjunction with a diagnostic algorithm, has the ability to predict the presence of IAI using a non-invasive, cervical vaginal swab-based immunodiagnostic test with a high degree of accuracy.

In one embodiment, the invention provides novel panels of biomarkers which can be measured and used to determine the presence or absence of IAI in a pregnant female mammalian subject.

In one aspect, the present invention provides a method for the diagnosis of intra-amniotic infection in a pregnant female mammalian subject comprising (a) measuring in a sample of cervical-vaginal fluid obtained from said subject the level of two or more proteins selected from the group consisting of growth regulated oncogene alpha (GRO-a), macrophage inflammatory protein 1 beta (MIP1b), alpha-1-acid glycoprotein (A1AG), alpha-fetoprotein (AFP), interleukin6 (IL-6), lipopolysaccharide binding protein (LBP), vascular cell adhesion molecule-1 (VCAM-1), monocyte chemotactic peptide-1 (MCP-1), beta-2-microglobulin (B2MG), and tissue inhibitor of metalloproteinases-1 (TIMP-1), relative to the level in normal cervical-vaginal fluid or cervical-vaginal fluid known to be indicative of intra-amniotic infection; and (b) diagnosing said subject with intra-amniotic infection if said level is determined to show a statistically significant difference relative to the level in said normal cervical-vaginal fluid, or is determined not to show a statistically significant difference relative to the level in said cervical-vaginal fluid known to be indicative of intra-amniotic infection. In one embodiment, the subject is a human patient. In certain embodiments, the method of the invention includes measuring the abundance of at least three, at least four, at least five, at least six, at least seven, at least eight, at least nine, or all of the proteins.

In one aspect, the present invention provides a method for the diagnosis of intra-amniotic infection in a pregnant female mammalian subject comprising (a) measuring in a sample of cervical-vaginal fluid obtained from said subject the levels of two or more proteins selected from the group consisting of growth regulated oncogene alpha (GRO-a), macrophage inflammatory protein 1 beta (MIP1b), alpha-1-acid glycoprotein (A1AG), alpha-fetoprotein (AFP), interleukin6 (IL-6), lipopolysaccharide binding protein (LBP), vascular cell adhesion molecule-1 (VCAM-1), monocyte chemotactic peptide-1 (MCP-1), beta-2-microglobulin (B2MG), and tissue inhibitor of metalloproteinases-1 (TIMP-1), relative to the corresponding levels of said two or more proteins in normal cervical-vaginal fluid or cervical-vaginal fluid known to be indicative of intra-amniotic infection; and (b) diagnosing said subject with intra-amniotic infection if each of said levels of each of said two or more proteins in said sample is determined to show a statistically significant difference relative to the corresponding levels of each of said proteins in normal cervical-vaginal fluid, or is determined not to show a statistically significant difference relative to the corresponding levels of each of said two or more proteins in said cervical-vaginal fluid known to be indicative of intra-amniotic infection. In one embodiment, the subject is a human patient. In certain embodiments, the method of the invention includes measuring the levels of at least three, at least four, at least five, at least six, at least seven, at least eight, at least nine, or all of the proteins.

In one embodiment, the biomarkers measured include growth regulated oncogene alpha (GRO-a) and macrophage inflammatory protein 1 beta (MIP1b). In another embodiment, the biomarkers measured include growth regulated oncogene alpha (GRO-a) and alpha-1-acid glycoprotein (A1AG). In yet another embodiment, the biomarkers measured include alpha-1-acid glycoprotein (A1AG) and macrophage inflammatory protein 1 beta (MIP1b). In these embodiments, further biomarkers measured may include alpha-fetoprotein (AFP), interleukin-6 (IL-6), lipopolysaccharide binding protein (LBP), vascular cell adhesion molecule-1 (VCAM-1), monocyte chemotactic peptide-1 (MCP-1), beta-2-microglobulin (B2MG), and/or tissue inhibitor of metalloproteinases-1 (TIMP-1). In further embodiments, the biomarkers measured may include IGF-binding protein-1 (IGFBP-1).

In certain embodiments, the biomarkers measured include tissue inhibitor of metalloproteinases-1 (TIMP-1) and growth regulated oncogene alpha (GRO-a). In certain embodiments, the biomarkers measured include tissue inhibitor of metalloproteinases-1 (TIMP1) and macrophage inflammatory protein 1 beta (MIP1b). In certain embodiments, the biomarkers measured include tissue inhibitor of metalloproteinases-1 (TIMP-1) and alpha-1-acid glycoprotein (A1AG). In these embodiments, further biomarkers measured may include interleukin-6 (IL-6).

In certain embodiments, the biomarkers measured include alpha-fetoprotein (AFP), interleukin-6 (IL-6) and macrophage inflammatory protein 1 beta (MIP1b). In certain embodiments, the biomarkers measured include interleukin-6 (IL-6), alpha-1-acid glycoprotein (A1AG), lipopolysaccharide binding protein (LBP), growth regulated oncogene alpha (GRO-a), and alpha-fetoprotein (AFP).

In one embodiment, methods of the invention include measuring the level of proteins of two or more proteins selected from the group consisting of macrophage inflammatory protein 1 beta (MIP1b), alpha-1-acid glycoprotein (A1AG), and tissue inhibitor of metalloproteinases-1 (TIMP-1), and diagnosing said subject with intra-amniotic infection, if two or more of said tested proteins shows a statistically significant difference in the cervical-vaginal fluid sample relative to normal cervical-vaginal fluid.

In one embodiment, methods of the invention include measuring the levels of each of two or more proteins selected from the group consisting of macrophage inflammatory protein 1 beta (MIP1b), alpha-1-acid glycoprotein (A1AG), and tissue inhibitor of metalloproteinases-1 (TIMP-1), and diagnosing said subject with intra-amniotic infection, if the level of each of the two or more of said tested proteins shows a statistically significant difference in the cervical-vaginal fluid sample relative to the corresponding protein level in normal cervical-vaginal fluid.

In certain embodiments, the methods of the invention include diagnosing the subject with intra-amniotic infection, if the levels of all of said tested proteins show a statistically significant difference in the cervical-vaginal fluid sample relative to the corresponding levels of said proteins in normal cervical-vaginal fluid. In all embodiments, the level of the proteins identified herein may be determined by an immunoassay. In certain embodiments, the levels of the proteins identified herein may be determined using a protein array. In certain embodiments, the levels of the proteins identified herein may be determined using an immunochromatographic test device. In certain embodiments using an immunochromatographic test device, the levels of the proteins identified herein may be determined using an immunochromatographic test device comprising one or more chromatography test strips. In certain embodiments using an immunochromatographic test device, the immunochromatographic test device is a lateral flow device.

In certain embodiments, the invention provides an immunochromatographic test device comprising two or more chromatography strips for the detection of two or more proteins selected from the group consisting of growth regulated oncogene alpha (GRO-a), macrophage inflammatory protein 1 beta (MIP1b), alpha-1-acid glycoprotein (A1AG), alpha-fetoprotein (AFP), interleukin-6 (IL-6), lipopolysaccharide binding protein (LBP), vascular cell adhesion molecule-1 (VCAM-1), monocyte chemotactic peptide-1 (MCP-1), beta-2-microglobulin (B2MG), and tissue inhibitor of metalloproteinases-1 (TIMP-1). In embodiments, the immunochromatographic test device comprises test strips comprising antibodies to two or more proteins selected from the group consisting of growth regulated oncogene alpha (GRO-a), macrophage inflammatory protein 1 beta (MIP1b), alpha-1-acid glycoprotein (A1AG), alpha-fetoprotein (AFP), interleukin-6 (IL-6), lipopolysaccharide binding protein (LBP), vascular cell adhesion molecule-1 (VCAM-1), monocyte chemotactic peptide-1 (MCP-1), beta-2-microglobulin (B2MG), and tissue inhibitor of metalloproteinases-1 (TIMP-1). In embodiments, the immunochromatographic test device is a lateral flow device.

In certain embodiments, the invention provides an immunochromatographic test device comprising three or more chromatography strips for the detection of three or more proteins selected from the group consisting of growth regulated oncogene alpha (GRO-a), macrophage inflammatory protein 1 beta (MIP1b), alpha-1-acid glycoprotein (A1AG), alpha-fetoprotein (AFP), interleukin-6 (IL-6), IGF binding protein-1 (IGFBP-1), lipopolysaccharide binding protein (LBP), vascular cell adhesion molecule-1 (VCAM-1), monocyte chemotactic peptide-1 (MCP-1), beta-2-microglobulin (B2MG), and tissue inhibitor of metalloproteinases-1 (TIMP-1). In embodiments, the immunochromatographic test device comprises test strips comprising antibodies to three or more proteins selected from the group consisting of growth regulated oncogene alpha (GRO-a), macrophage inflammatory protein 1 beta (MIP1b), alpha-1-acid glycoprotein (A1AG), alpha-fetoprotein (AFP), interleukin-6 (IL-6), IGF binding protein-1 (IGFBP-1), lipopolysaccharide binding protein (LBP), vascular cell adhesion molecule-1 (VCAM-1), monocyte chemotactic peptide-1 (MCP-1), beta-2-microglobulin (B2MG), and tissue inhibitor of metalloproteinases-1 (TIMP-1). In embodiments, the immunochromatographic test device is a lateral flow device.

In another aspect, the present invention provides a method for the diagnosis of intra-amniotic infection in a pregnant female mammalian subject comprising:
(a) obtaining a sample of cervical-vaginal fluid from said subject; (b) determining the level of two or more proteins selected from the group consisting of growth regulated oncogene alpha (GRO-a), macrophage inflammatory protein 1 beta (MIP1b), alpha-1-acid glycoprotein (A1AG), alpha-fetoprotein (AFP), interleukin-6 (IL-6), lipopolysaccharide binding protein (LBP), vascular cell adhesion molecule-1 (VCAM-1), monocyte chemotactic peptide-1 (MCP-1), beta-2-microglobulin (B2MG), and tissue inhibitor of metalloproteinases-1 (TIMP-1), relative to the corresponding levels of each of said two or more proteins in normal cervical-vaginal fluid or cervical-vaginal fluid known to be indicative of intra-amniotic infection; and diagnosing said subject with intra-amniotic infection if said levels of each of said two or more proteins is determined to show a statistically significant difference relative to the corresponding levels of each of said two or more proteins in said normal cervical-vaginal fluid, or is determined not to show a statistically significant difference relative to the corresponding levels of each of said two or more proteins in said cervical-vaginal fluid known to be indicative of intra-amniotic infection.

In another aspect, the invention provides methods for determining signs and symptoms indicating intra-amniotic infection comprising
(a) measuring in a sample of cervical-vaginal fluid obtained from said subject the level of two or more proteins selected from the group consisting of growth regulated oncogene alpha (GRO-a), macrophage inflammatory protein 1 beta (MIP1b), alpha-1-acid glycoprotein (A1AG), alpha-fetoprotein (AFP), interleukin-6 (IL-6), lipopolysaccharide binding protein (LBP), vascular cell adhesion molecule-1 (VCAM-1), monocyte chemotactic peptide-1 (MCP-1), beta-2-microglobulin (B2MG), and tissue inhibitor of metalloproteinases-1 (TIMP-1), relative to the level in normal cervical-vaginal fluid or cervical-vaginal fluid known to be indicative of intra-amniotic infection; and (b) diagnosing said subject with intra-amniotic infection if said level is determined to show a statistically significant difference relative to the level in said normal cervical-vaginal fluid, or is determined not to show a statistically significant difference relative to the level in said cervical-vaginal fluid known to be indicative of intra-amniotic infection. In certain embodiments, the signs and symptoms include, but are not limited to, maternal fever ($\geq 37.8°$ C.), maternal leukocytosis ($\geq 15,000/mm^3$), maternal and/or fetal tachycardia, uterine tenderness, and/or foul-smelling amniotic fluid.

In another aspect, the invention provides methods for determining signs and symptoms indicating intra-amniotic infection comprising (a) measuring in a sample of cervical-vaginal fluid obtained from said subject the levels of two or more proteins selected from the group consisting of growth regulated oncogene alpha (GRO-a), macrophage inflammatory protein 1 beta (MIP1b), alpha-1-acid glycoprotein (A1AG), alpha-fetoprotein (AFP), interleukin-6 (IL-6), lipopolysaccharide binding protein (LBP), vascular cell adhesion molecule-1 (VCAM-1), monocyte chemotactic peptide-1 (MCP-1), beta-2-microglobulin (B2MG), and tissue inhibitor of metalloproteinases-1 (TIMP-1), relative to the corresponding levels of said two or more proteins in normal cervical-vaginal fluid or relative to the corresponding levels of said two or more proteins in cervical-vaginal fluid known to be indicative of intra-amniotic infection; and (b) diagnosing said subject with intra-amniotic infection if each of said levels of said two or more proteins in said sample is determined to show a statistically significant difference relative to the corresponding levels of each of said two or more proteins in said normal cervical-vaginal fluid, or is determined not to show a statistically significant difference relative to the corresponding levels of each of said two or more proteins in said cervical-vaginal fluid known to be indicative of intra-amniotic infection. In certain embodiments, the signs and symptoms include, but are not limited to, maternal fever ($\geq 37.8°$ C.), maternal leukocytosis ($\geq 15,000/mm^3$), maternal and/or fetal tachycardia, uterine tenderness, and/or foul-smelling amniotic fluid.

In one aspect, the invention concern a method for the diagnosis of intra-amniotic infection in a pregnant female mammalian subject comprising:

(a) testing in a sample of cervical-vaginal fluid obtained from said subject the levels of $\alpha$-fetoprotein (AFP), interleukin-6 (IL-6) and IGF binding protein-1 (IGFBP-1); and (b) diagnosing said subject with intra-amniotic infection if each of said levels of AFP, IL-6, and IGFBP-1 in said sample is determined to show a statistically significant difference relative to the corresponding levels of AFP, IL-6, and IGFBP-1 in normal cervical-vaginal fluid, or is determined not to show a statistically significant difference relative to the corresponding levels of each of AFP, IL-6, and IGFBP-1 in cervical-vaginal fluid known to be indicative of intra-amniotic infection.

In one embodiment the subject is a human patient.

In another embodiment testing is implemented using an apparatus adapted to determine the level of the proteins.

In yet another embodiment testing is performed by using a software program executed by a suitable processor.

In a further embodiment, the program is embodied in software stored on a tangible medium.

In a still further embodiment, the tangible medium is selected from the group consisting of a flash drive, a CD-ROM, a floppy disk, a hard drive, a DVD, and a memory associated with the processor.

In a different embodiment, the method further comprises the step of preparing a report recording the results of said testing or the diagnosis, where the report may be recorded or stored on a tangible medium, such as paper, a flash drive, a CD-ROM, a floppy disk, a hard drive, a DVD, or a memory associated with the processor.

In another embodiment, the method further comprises the step of communicating the results of said diagnosis to an interested party, such as the patient or the attending physician. In various embodiments, the communication is in writing, by email, or by telephone.

In yet another embodiment, the protein levels are determined by an immunoassay.

In a further embodiment, the protein levels are determined by an immunochromatographic test, which may employ a lateral flow device.

In still further embodiments, the protein levels are determined by mass spectrometry or by using a protein array.

In another aspect, the invention concerns an immunoassay kit comprising antibodies and reagents for the detection of $\alpha$-fetoprotein (AFP), interleukin-6 (IL-6) and IGF binding protein-1 (IGFBP-1).

In yet another aspect, the invention concerns an immunochromatographic test device comprising one or more chromatography strips for the detection of $\alpha$-fetoprotein (AFP), interleukin-6 (IL-6) and IGF binding protein-1 (IGFBP-1).

In one embodiment, in the immunochromatographic test device the test strip or test strips comprise(s) antibodies to $\alpha$-fetoprotein (AFP), interleukin-6 (IL-6) and IGF binding protein-1 (IGFBP-1).

In another embodiment, the immunochromatographic test device is a lateral flow device.

In a further aspect, the invention concerns a report comprising the results of and/or diagnosis based on a test comprising (a) testing in a sample of cervical-vaginal fluid obtained from said subject the levels of $\alpha$-fetoprotein (AFP), interleukin-6 (IL-6) and IGF binding protein-1 (IGFBP-1); and (b) diagnosing said subject with intra-amniotic infection if said level is determined to show a statistically significant difference relative to the level in normal cervical-vaginal fluid, or is determined not to show a statistically significant difference relative to the level in cervical-vaginal fluid known to be indicative of intra-amniotic infection.

In a further aspect, the invention concerns a report comprising the results of and/or diagnosis based on a test comprising (a) testing in a sample of cervical-vaginal fluid obtained from said subject the levels of $\alpha$-fetoprotein (AFP), interleukin-6 (IL-6) and IGF binding protein-1 (IGFBP-1); and (b) diagnosing said subject with intra-amniotic infection if each of said levels of AFP, IL-6 and IGFBP-1 is determined to show a statistically significant difference relative to the corresponding level of AFP, IL-6 and IGFBP-1 in normal cervical-vaginal fluid, or is determined not to show a statistically significant difference relative to the corresponding level of AFP, IL-6 and IGFBP-1 in cervical-vaginal fluid known to be indicative of intra-amniotic infection.

In a still further aspect, the invention concerns a tangible medium storing the results of and/or diagnosis based on a test comprising (a) testing in a sample of cervical-vaginal fluid obtained from said subject the level of α-fetoprotein, interleukin-6 (IL-6) and IGF binding protein-1 (IGFBP-1); and (b) diagnosing said subject with intra-amniotic infection if said level is determined to show a statistically significant difference relative to the level in normal cervical-vaginal fluid, or is determined not to show a statistically significant difference relative to the level in cervical-vaginal fluid known to be indicative of intra-amniotic infection.

In certain embodiments, the measuring is implemented using an apparatus adapted to determine the level of said proteins. In another embodiment, the measuring is performed by using a software program executed by a suitable processor. In certain embodiments, the program is embodied in software stored on a tangible medium. In certain other embodiments, the tangible medium is selected from the group consisting of a CD-ROM, a floppy disk, a hard drive, a DVD, and a memory associated with the processor.

In certain embodiments, the methods of the invention further include a step of preparing a report recording the results of the testing or the diagnosis. In one embodiment, the report is recorded or stored on a tangible medium. In a specific embodiment, the tangible medium is paper. In another embodiment, the tangible medium is selected from the group consisting of a CD-ROM, a floppy disk, a hard drive, a DVD, and a memory associated with the processor.

In certain other embodiments, the methods of the invention further include a step of communicating the results of said diagnosis to an interested party. In one embodiment, the interested party is the patient or the attending physician. In another embodiment, the communication is in writing, by email, or by telephone.

In another aspect, the present invention provides an immunoassay kit comprising antibodies and reagents for the detection of two or more proteins selected from the group consisting of growth regulated oncogene alpha (GRO-a), macrophage inflammatory protein 1 beta (MIP1b), alpha-1-acid glycoprotein (A1AG), alpha-fetoprotein (AFP), interleukin-6 (IL-6), lipopolysaccharide binding protein (LBP), vascular cell adhesion molecule-1 (VCAM-1), monocyte chemotactic peptide-1 (MCP-1), beta-2-microglobulin (B2MG), and tissue inhibitor of metalloproteinases-1 (TIMP-1). In one embodiment, the immunoassay kit includes antibodies and reagents for the detection of all of the proteins identified herein.

In another aspect, the present invention provides an immunoassay kit comprising antibodies and reagents for the detection of two or more proteins selected from the group consisting of growth regulated oncogene alpha (GRO-a), macrophage inflammatory protein 1 beta (MIP1b), alpha-1-acid glycoprotein (A1AG), alpha-fetoprotein (AFP), interleukin-6 (IL-6), IGF binding protein-1 (IGFBP-1), lipopolysaccharide binding protein (LBP), vascular cell adhesion molecule-1 (VCAM-1), monocyte chemotactic peptide-1 (MCP-1), beta-2-microglobulin (B2MG), and tissue inhibitor of metalloproteinases-1 (TIMP-1). In one embodiment, the immunoassay kit includes antibodies and reagents for the detection of all of the proteins identified herein.

In yet another aspect, the present invention provides an immunoassay kit comprising antibodies and reagents for the detection of two or more proteins selected from the group consisting of macrophage inflammatory protein 1 beta (MIP1b), alpha-1-acid glycoprotein (A1AG), and tissue inhibitor of metalloproteinases-1 (TIMP-1).

In still another aspect, the present invention provides a report comprising the results of and/or diagnosis based on a test comprising (a) measuring in a sample of cervical-vaginal fluid obtained from said subject the level of two or more proteins selected from the group consisting of growth regulated oncogene alpha (GRO-a), macrophage inflammatory protein 1 beta (MIP1b), alpha-1-acid glycoprotein (A1AG), alpha-fetoprotein (AFP), interleukin-6 (IL-6), lipopolysaccharide binding protein (LBP), vascular cell adhesion molecule-1 (VCAM-1), monocyte chemotactic peptide-1 (MCP-1), beta-2-microglobulin (B2MG), and tissue inhibitor of metalloproteinases-1 (TIMP-1), relative to the level in normal cervical-vaginal fluid or cervical-vaginal fluid known to be indicative intra-amniotic infection; and (b) diagnosing said subject with intra-amniotic infection if said level is determined to show a statistically significant difference relative to the level in said normal cervical-vaginal fluid, or is determined not to show a statistically significant difference relative to the level in said cervical-vaginal fluid known to be indicative of intra-amniotic infection.

In another aspect, the present invention provides a tangible medium storing the results of and/or diagnosis based on a test comprising (a) measuring in a sample of cervical-vaginal fluid obtained from said subject the level of two or more proteins selected from the group consisting of growth regulated oncogene alpha (GRO-a), macrophage inflammatory protein 1 beta (MIP1b), alpha-1-acid glycoprotein (A1AG), alpha-fetoprotein (AFP), interleukin-6 (IL-6), lipopolysaccharide binding protein (LBP), vascular cell adhesion molecule-1 (VCAM-1), monocyte chemotactic peptide-1 (MCP-1), beta-2-microglobulin (B2MG), and tissue inhibitor of metalloproteinases-1 (TIMP-1), relative to the level in normal cervical-vaginal fluid or cervical-vaginal fluid known to be indicative of intra-amniotic infection; and (b) diagnosing said subject with intra-amniotic infection if said level is determined to show a statistically significant difference relative to the level in said normal cervical-vaginal fluid, or is determined not to show a statistically significant difference relative to the level in said cervical-vaginal fluid known to be indicative of intra-amniotic infection.

DETAILED DESCRIPTION OF THE INVENTION

Definitions

Figure 1:
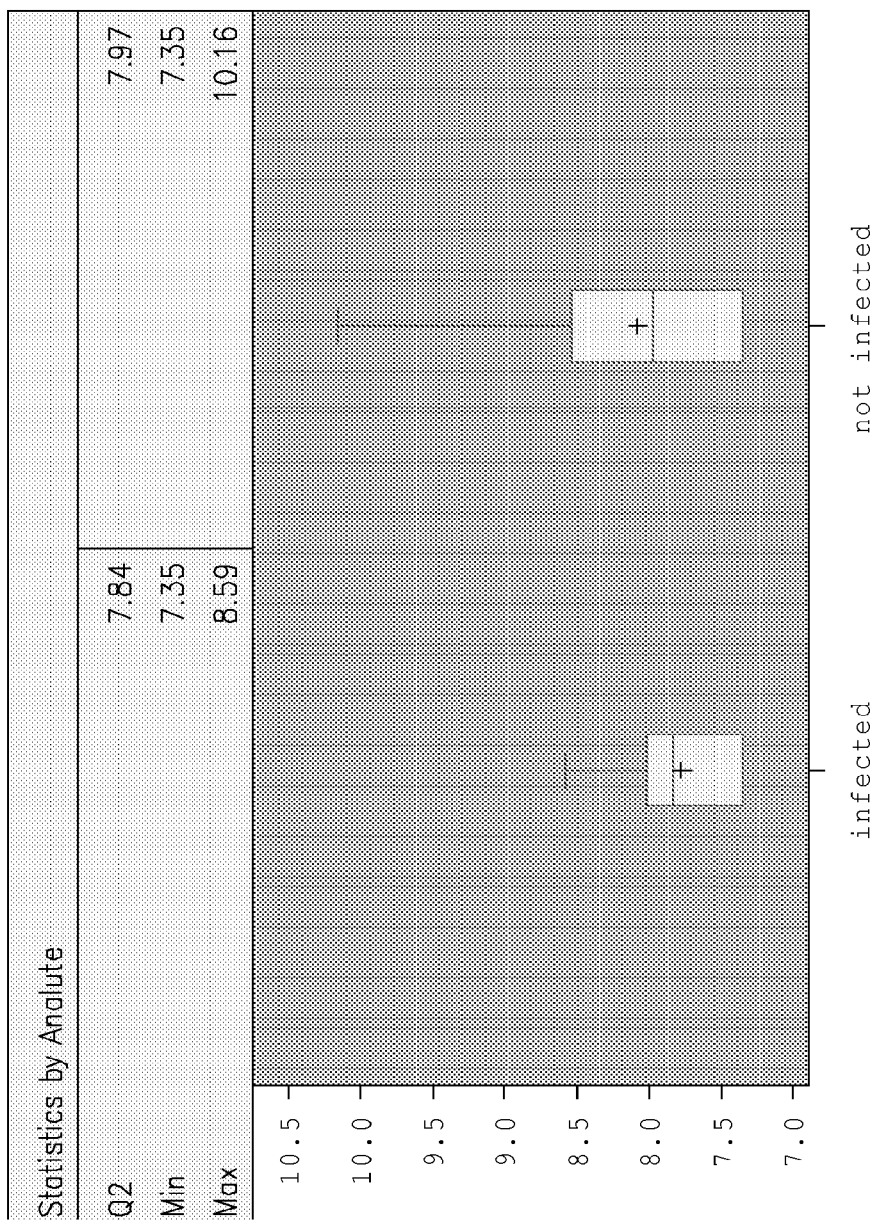
FIG. 1 depicts boxplots showing natural logarithm value of GROalpha (Assay 1) in IAI infected (n=14) vs. non-infected patients (n=95).

It is to be understood that this invention is not limited to particular embodiments, which can, of course, vary. It is also to be understood that the terminology used herein is for the purpose of describing particular embodiments only, and is not intended to be limiting. As used in this specification and the appended claims, terms in the singular and the singular forms "a," "an" and "the," for example, optionally include plural referents unless the content clearly dictates otherwise. Thus, for example, reference to "a probe" optionally includes a plurality of probe molecules; similarly, depending on the context, use of the term "a nucleic acid" optionally includes, as a practical matter, many copies of that nucleic acid molecule. Letter designations for genes or proteins can refer to the gene form and/or the protein form, depending on context. One of skill is fully able to relate the nucleic acid and amino acid forms of the relevant biological molecules by reference to the sequences herein, known sequences and the genetic code.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994) provides one skilled in the art with a general guide to many of the terms used in the present application.

The terms "corresponds" and "corresponding" and grammatical equivalents are used herein to refer to analogous or like substances; for example, when referring to two mixtures of proteins, protein A in the first mixture corresponds to, and is the corresponding protein of, protein A in the second mixture; protein B in the first mixture corresponds to, and is the corresponding protein of, protein B in the second mixture; and so on.

The term "proteome" is used herein to describe a significant portion of proteins in a biological sample at a given time. The concept of proteome is fundamentally different from the genome. While the genome is virtually static, the proteome continually changes in response to internal and external events.

The term "proteomic profile" is used to refer to a representation of the expression pattern of a plurality of proteins in a biological sample, e.g. a biological fluid at a given time. The proteomic profile can, for example, be represented as a mass spectrum, but other representations based on any physicochemical or biochemical properties of the proteins are also included. Thus the proteomic profile may, for example, be based on differences in the electrophoretic properties of proteins, as determined by two-dimensional gel electrophoresis, e.g. by 2-D PAGE, and can be represented, e.g. as a plurality of spots in a two-dimensional electrophoresis gel. Differential expression profiles may have important diagnostic value, even in the absence of specifically identified proteins. Single protein spots can then be detected, for example, by immunoblotting, multiple spots or proteins using protein microarrays. The proteomic profile typically represents or contains information that could range from a few peaks to a complex profile representing 50 or more peaks. Thus, for example, the proteomic profile may contain or represent at least 2, or at least 5 or at least 10 or at least 15, or at least 20, or at least 25, or at least 30, or at least 35, or at least 40, or at least 45, or at least 50, or at least 60, or at least 65, or at least 70, or at least 75, or at least 80, or at least 85, or at least 85, or at least 90, or at least 95, or at least 100, or at least 125, or at least 150, or at least 175, or at least 200 proteins.

The term "pathologic condition" is used in the broadest sense and covers all changes and phenomena that compromise the well-being of a subject. Pathologic maternal conditions include, without limitation, intra-amniotic infection, conditions of fetal or maternal origin, such as, for example preeclampsia, and preterm labor and delivery. Pathologic fetal conditions include, without limitation, chromosomal defects (aneuploidies), such as Down syndrome, and all abnormalities in gestational age and fetal maturity.

The term "state of a pathologic [maternal or fetal] condition" is used herein in the broadest sense and refers to the absence, presence, extent, stage, nature, progression or regression of the pathologic condition.

The term "unique expression signature" is used to describe a unique feature or motif within the proteomic profile of a biological sample (e.g. a reference sample) that differs from the proteomic profile of a corresponding normal biological sample (obtained from the same type of source, e.g. biological fluid) in a statistically significant manner.

The terms "intra-amniotic infection (IAI)," "amniotic fluid infection," "amnionitis," and "clinical chorioamnionitis" are used interchangeably, and refer to an acute infection, including, but not restricted to bacterial, of the amniotic fluid and intrauterine contents during pregnancy.

"Patient response" can be assessed using any endpoint indicating a benefit to the patient, including, without limitation, (1) inhibition, at least to some extent, of the progression of a pathologic condition, (2) prevention of the pathologic condition, (3) relief, at least to some extent, of one or more symptoms associated with the pathologic condition; (4) increase in the length of survival following treatment; and/or (5) decreased mortality at a given point of time following treatment.

The term "treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Congenital malformation" is an abnormality which is non-hereditary but which exists at birth.

The designation of any particular protein, as used herein, includes all fragments, precursors, and naturally occurring variants, such as alternatively spliced and allelic variants and isoforms, as well as soluble forms of the protein named, along with native sequence homologs (including all naturally occurring variants) in other species. Thus, for example, when it is stated that the abundance of macrophage inflammatory protein 1 beta (Swiss-Prot Acc. No. P13236) is tested, the statement specifically includes testing any fragments, precursors, or naturally occurring variant of the protein listed under Swiss-Prot Acc. No. 13236, as well as its non-human homologs and naturally occurring variants thereof, if subject is non-human.

Detailed Description

The present invention concerns methods and means for an early, reliable and non-invasive testing of maternal and fetal conditions based upon the proteomic profile of a biological fluid of the mother or fetus. In particular, the present invention is based upon the discovery of protein markers that are differentially present in samples of IAI patients and control subjects, and the application of this discovery in methods and kits for determining the presence or absence of IAI. These protein markers are found in samples from IAI patients at levels that are different than the levels in samples from patients without IAI. Accordingly, the amount of two or more markers found in a test sample compared to a control, or the presence or absence of two or more markers in the test sample provides useful information regarding the IAI status of the patient.

The present invention also concerns methods and means for early, reliable and non-invasive testing of maternal and fetal conditions based upon the proteomic profile of a biological fluid of the mother or fetus. In particular, the present invention provides diagnostic and prognostics tests for early and reliable detection of IAI by measuring alpha-fetoprotein (α-fetoprotein), interleukin-6 (IL-6) and insulin growth factor binding protein-1 (IGFBP-1) in a biological fluid, such as cervical vaginal fluid (CVF), obtained from a pregnant woman or fetus.

The invention is further based on the discovery that incorporation of the subject's signs and symptoms, e.g., maternal fever ($\geq 37.8°$ C.), maternal leukocytosis ($\geq 15,000/mm^3$), maternal or fetal tachycardia, uterine tenderness, or foul-smelling amniotic fluid, into the diagnostic algorithm is useful in the determination of whether IAI is present or absent.

The invention utilizes proteomics techniques well known in the art, as described, for example, in the following textbooks, the contents of which are hereby expressly incorporated by reference: Proteome Research: New Frontiers in Functional Genomics (Principles and Practice), M. R. Wilkins et al., eds., Springer Verlag, 1007; 2-D Proteome Analysis Protocols, Andrew L Link, editor, Humana Press, 1999; Proteome Research: Two-Dimensional Gel Electrophoresis and Identification Methods (Principles and Practice), T. Rabilloud editor, Springer Verlag, 2000; Proteome Research: Mass Spectrometry (Principles and Practice), P. James editor, Springer Verlag, 2001; Introduction to Proteomics, D. C. Liebler editor, Humana Press, 2002; Proteomics in Practice: A Laboratory Manual of Proteome Analysis, R. Westermeier et al., eds., John Wiley & Sons, 2002.

One skilled in the art will recognize many methods and materials similar or equivalent to those described herein, which could be used in the practice of the present invention. Indeed, the present invention is in no way limited to the methods and materials described.

1. Identification of Proteins and Polypeptides Expressed in Biological Fluids

According to the present invention, proteomics analysis of biological fluids can be performed using a variety of methods known in the art. Biological fluids include, for example, cervical-vaginal fluid (CVF), cord blood, neonatal serum, cerebrospinal fluid (CSF), amniotic fluid, serum, plasma, urine, cerebrospinal fluid, breast milk, mucus, saliva, and sweat.

Typically, protein patterns (proteome maps) of samples from different sources, such as normal biological fluid (normal sample) and a test biological fluid (test sample), are compared to detect proteins that are up- or down-regulated in a disease. These proteins can then be excised for identification and full characterization, e.g. using immunoassays, peptide-mass fingerprinting and/or mass spectrometry and sequencing methods, or the normal and/or disease-specific proteome map can be used directly for the diagnosis of the disease of interest, or to confirm the presence or absence of the disease.

In comparative analysis, it is important to treat the normal and test samples exactly the same way, in order to correctly represent the relative level or abundance of proteins, and obtain accurate results. The required amount of total proteins will depend on the analytical technique used, and can be readily determined by one skilled in the art. The proteins present in the biological samples are typically separated by two-dimensional gel electrophoresis (2-DE) according to their pI and molecular weight. The proteins are first separated by their charge using isoelectric focusing (one-dimensional gel electrophoresis). This step can, for example, be carried out using immobilized pH-gradient (IPG) strips, which are commercially available. The second dimension is a normal SDS-PAGE analysis, where the focused IPG strip is used as the sample. After 2-DE separation, proteins can be visualized with conventional dyes, like Coomassie Blue or silver staining, and imaged using known techniques and equipment, such as, e.g. Bio-Rad 10 GS-800™ densitometer and PDQUEST™ software, both of which are commercially available.

Individual spots are then cut from the gel, destained, and subjected to tryptic digestion. The peptide mixtures can be analyzed by mass spectrometry (MS). Alternatively, the peptides can be separated, for example by capillary high pressure liquid chromatography (HPLC) and can be analyzed by MS either individually, or in pools.

Mass spectrometers consist of an ion source, mass analyzer, ion detector, and data acquisition unit. First, the peptides are ionized in the ion source. Then the ionized peptides are separated according to their mass-to-charge ratio in the mass analyzer and the separate ions are detected. Mass spectrometry has been widely used in protein analysis, especially since the invention of matrix-assisted laser-desorption ionisation/time-of-flight (MALDI-TOF) and electrospray ionisation (ESI) methods. There are several versions of mass analyzer, including, for example, MALDI-TOF and triple or quadrupole-TOF, or ion trap mass analyzer coupled to ESI. Thus, for example, a Q-T of-2 mass spectrometer utilizes an orthogonal time-of-flight analyzer that allows the simultaneous detection of ions across the full mass spectrum range. For further details see, e.g. Chernusevich et al., *J. Mass Spectrom.* 36:849-865 (2001). If desired, the amino acid sequences of the peptide fragments and eventually the proteins from which they derived can be determined by techniques known in the art, such as certain variations of mass spectrometry, or Edman degradation.

2. Early Detection of Intra-Amniotic Infection and Related Complications

Intra-amniotic infection (IAI) is an acute bacterial infection of the amniotic fluid and intrauterine contents during pregnancy. Prospective studies indicate that IAI occurs in 4% to 10% of all deliveries (Newton, E. R., Prihoda, T. J., and Gibbs, R. S.: Logistic regression analysis of risk factors for intra-amniotic infection. Obstet. Gynecol. 73:571, 1989; Soper, D. E., Mayhall, C. G., and Dalton, H. P.: Risk factors for intraamniotic infection: a prospective epidemicologic study. American Journal of Obstetrics and Gynecology 161: 562, 1989; and Lopez-Zeno, J. A., Peaceman, A. M., Adashek, J. A., and Socol, M. L.: A controlled trial of a program for the active management of labor. N. Engl. J. Med. 326:450, 1992). Other terms used to describe IAI include amniotic fluid infection, amnionitis, and clinical chorioamnionitis. Intra-amniotic infection is clinically diagnosed by maternal fever, uterine tenderness, leukocytosis, and fetal tachycardia and should be distinguished from histologic chorioamnionitis. Intra-amniotic infection is an important cause of maternal and neonatal morbidity. Intra-amniotic infection accounts for 10-40% of cases of febrile morbidity in the peripartum period and is associated with 20-40% of cases of early neonatal sepsis and pneumonia (Newton, E. R.: Chorioamnionitis and intraamniotic infection. Clin. Obstet. Gynecol. 36:795, 1993). Maternal bacteremia occurs in 2-6% of patients with IAI and postpartum infectious morbidity is increased. There is also an increased risk of dysfunctional labor and cesarean delivery among patients with IAI. Duff et al. reported a 75% incidence of dysfunctional labor and a 34% incidence of cesarean delivery among patients who developed intra-amniotic infection while in labor (Duff, P., Sanders, R., and Gibbs, R. S.: The course of labor in term pregnancies with chorioamnionitis. American Journal of Obstetrics and Gynecology 147:391, 1983). Intra-amniotic infection is also associated with increased neonatal morbidity and mortality, particularly among preterm neonates. In general, there is a three to four-fold increase in perinatal mortality among low birth weight neonates born to mothers with IAI (Gibbs, R. S., Castillo, M. A., and Rodgers, P. J.: Management of Acute Chorioamnionitis. American Journal of Obstetrics and Gynecology 136:709, 1980; Gilstrap, L. C., III, Leveno, K. J., Cox, S. M., Burris, J. S., Mashburn, M., and Rosenfeld, C. R.: Intrapartum treatment of acute chorioamnionitis: impact on neonatal sepsis. Am. J. Obstet. Gynecol. 159:579, 1988). There are also increases in respiratory distress syndrome, intraventricular hemorrhage, and neonatal sepsis Morales, W. J.: The effect of chorioamnionitis on the developmental outcome of preterm infants at one year. Obstetrics and Gynecology 70:183, 1987). Recently, IAI has been implicated in neonatal periventricular leukomalacia and cerebral palsy; the risks of cerebral white matter damage and cerebral palsy are nine-fold greater in the setting of intra-amniotic infection Bejar, R., Wozniak, P., Allard, M., Benirschke, K., Vaucher, Y., Coen, R., Berry, C., Schragg, P., Villegas, I., and Resnik, R.: Antenatal origin of neurologic damage in newborn infants. I. Preterm infants. Am. J. Obstet. Gynecol. 159: 357, 1988; Grether, J. K. and Nelson, K. B.: Maternal infection and cerebral palsy in infants of normal birth weight. JAMA 278:207, 1997). Finally, subclinical IAI has been found in at least 10% of women in preterm labor with intact fetal membranes, suggesting that IAI is an important, and potentially preventable, cause of prematurity (Romero, R., Avila, C., Brekus, C. A., and Morotti, R.: The role of systemic and intrauterine infection in preterm parturition. Annuals of the New York Academy of Sciences 622:355, 1991). A literature review by Newton demonstrated incidences of clinical IAI of 41% at gestational ages less than 27 weeks, 15% at gestational ages of 27-37 weeks, and 2% at gestations of 38 weeks or greater (Newton et al., supra). Bacteria indigenous to the lower genital tract have also been recovered from the amniotic fluid of 10-20% of all women in preterm labor with intact fetal membranes without clinical signs of intra-amniotic infection (Romero et al., supra), and in up to 67% of women in preterm labor with pregnancies ending at 23-24 weeks (Watts, D. H., Krohn, M. A., Hillier, S. L., and Eschenbach, D. A.: The association of occult amniotic fluid infection with gestational age and neonatal outcome among women in preterm labor. Obstet Gynecol 79:351, 1992). Most of these patients deliver rapidly, and clinically apparent IAI develops in many. These observations support the hypothesis that ascending, initially subclinical intrauterine infections precede preterm labor and may be an important cause of extreme preterm deliveries.

Preterm delivery is defined as birth prior to the $37^{th}$ completed week of gestation. The incidence of preterm birth in the United States is 10-11% of all live births, and is increasing despite aggressive treatment of preterm labor. Overall, prematurity and its consequences are responsible for 80% of perinatal deaths not attributable to congenital malformations and add approximately $5 billion annually to the national health care budget. Risk factors for preterm birth include non-white race, young age, low socioeconomic status, maternal weight below 55 kg, nulliparity, first trimester bleeding, multiple gestations (Meis P J, Michielutte R, Peters T J, et al. Factors associated with preterm birth in Cardiff, Wales: II. Indicated and spontaneous preterm birth. Am J Obstet Gynecol 173:597-602, 1995).

Unfortunately the prediction of patients at risk for spontaneous preterm birth has been generally disappointing (Creasy R K, Jams J D. Preterm labor and delivery. In Maternal-Fetal Medicine, Creasy R K, Resnik R (eds.). W.B. Saunders Company, Philadelphia, Pa. 4th edition, 1999. Pages 498-531). Previous attempts at defining the population at greatest risk for preterm birth, and thereby potentially benefiting from early intervention have included risk-scoring indices, biochemical detection of cervical fetal fibronectin, ultrasound measurement of cervical length, and home uterine activity monitoring. These programs have been both costly, and have been hampered by the inability to predict with accuracy which patients might benefit from early intervention or prophylaxis. All suffer from poor positive predictive value of approximately 30%, with the majority of patients identified as "at risk" delivering at term. Interventions, including pharmacologic treatment to inhibit uterine contractions, are efficacious, but depend upon the early and reliable diagnosis of preterm labor. Early and reliable markers to identify patients at greatest risk for preterm birth are therefore necessary to reduce the tremendous costs and neonatal mortality and morbidity associated with preterm birth.

3. Early Detection and Diagnosis of Intra-Amniotic Infection Using Biomarkers in Biological Fluids A) The present invention provides an early and reliable, non-invasive method for the diagnosis of the intra-amniotic infection by proteomic analysis of biological fluids, such as, for example, cervical-vaginal fluid (CVF), amniotic fluid, serum, plasma, urine, cerebrospinal fluid, breast milk, mucus, or saliva. In one embodiment, the invention provides an early and reliable, non-invasive method for the diagnosis of the intra-amniotic infection by immunoassay or a panel of immunoassays. In one embodiment, the invention provides an early and reliable, non-invasive method for the diagnosis of the intra-amniotic infection by proteomic analysis of CVF.

By way of non-limiting example, the present invention provides methods for the diagnosis of intra-amniotic infection in a pregnant female subject comprising testing in a maternal cervical vaginal fluid sample obtained from said subject the level or amount of one of more proteins selected from the group consisting of growth regulated oncogene alpha (GRO-a), macrophage inflammatory protein 1 beta (MIP1b), alpha-1-acid glycoprotein (A1AG), alpha-fetoprotein (AFP), interleukin-6 (IL-6), lipopolysaccharide binding protein (LBP), vascular cell adhesion molecule-1 (VCAM-1), monocyte chemotactic peptide-1 (MCP-1), beta-2-microglobulin (B2MG), and tissue inhibitor of metalloproteinases-1 (TIMP-1). Diagnosis of intra-amniotic infection may be based on the statistically significant difference in the level, amount, or abundance of said proteins in patient specimens that are defined as positive for TAT versus control specimens that do not have TAT. In certain embodiments, diagnosis of intra-amniotic infection may be enhanced by incorporating into the diagnostic algorithm the signs and symptoms of the subject. For example, incorporation of signs and symptoms including, but not limited to, maternal fever ($\geq 37.8°$ C.), maternal leukocytosis ($\geq 15,000/mm^3$), maternal and/or fetal tachycardia, uterine tenderness, and/or foul-smelling amniotic fluid, may be included in the diagnostic algorithm.

TABLE 1

Biomarkers for IAI

| Accession | ID | Protein | SEQ ID NO |
|---|---|---|---|
| P09341 | GRO-a | growth regulated oncogene alpha | 1 |
| P13236 | MIP1b | macrophage inflammatory protein 1 beta | 2 |
| P02763 | A1AG | alpha-1-acid glycoprotein | 3 |
| P02771 | AFP | alpha-fetoprotein | 4 |
| P05231 | IL-6 | interleukin-6 | 5 |
| P18428 | LBP | lipopolysaccharide binding protein | 6 |
| P19320 | VCAM-1 | vascular cell adhesion molecule-1 | 7 |
| P13500 | MCP-1 | monocyte chemotactic peptide-1 | 8 |
| P61769 | B2MG | beta-2-microglobulin | 9 |
| P01033 | TIMP-1 | tissue inhibitor of metalloproteinases-1 | 10 |

As noted above, in the context of the present invention the term "proteomic profile" is used to refer to a representation of the expression pattern of a plurality of proteins in a biological sample, e.g. a biological fluid at a given time. The proteomic profile can, for example, be represented as a panel of immunoassay results, but other representations based on any physicochemical or biochemical properties of the proteins are also included. Although it is possible to identify and sequence all or some of the proteins present in the proteome of a biological fluid, this is not necessary for the diagnostic use of the proteomic profiles generated in accordance with the present invention. Diagnosis of a particular disease can be based on characteristic differences (unique expression signatures) between a normal proteomic profile, and proteomic profile of the same biological fluid obtained under the same circumstances, when the disease or pathologic condition to be diagnosed is present. The unique expression signature can be any unique feature or motif within the proteomic profile of a test or reference biological sample that differs from the proteomic profile of a corresponding normal biological sample obtained from the same type of source, in a statistically significant manner. When the proteomic profile of the test sample obtained from a mammalian subject is compared with the proteomic profile of a reference sample comprising a unique expression signature characteristic of a pathologic maternal or fetal condition, the mammalian subject is diagnosed with such pathologic condition if it shares the unique expression signature with the reference sample.

A particular pathologic maternal/fetal condition can be diagnosed by comparing the proteomic profile of a biological fluid obtained from the subject to be diagnosed with the proteomic profile of a normal biological fluid of the same kind, obtained and treated the same manner. If the proteomic profile of the test sample is essentially the same as the proteomic profile of the normal sample, the subject is considered to be free of the subject pathologic maternal/fetal condition. If the proteomic profile of the test sample shows a unique expression signature relative to the proteomic profile of the normal sample, the subject is diagnosed with the maternal/fetal condition in question.

Alternatively or in addition, the proteomic profile of the test sample may be compared with the proteomic profile of a reference sample, obtained from a biological fluid of a subject independently diagnosed with the pathologic maternal/fetal condition in question. In this case, the subject is diagnosed with the pathologic condition if the proteomic profile of the test sample shares at least one feature, or a combination of features representing a unique expression signature, with the proteomic profile of the reference sample.

In the methods of the present invention the proteomic profile of a normal biological sample plays an important diagnostic role. As discussed above, if the proteomic profile of the test sample is essentially the same as the proteomic profile of the normal biological sample, the patient is diagnosed as being free of the pathologic maternal/fetal condition to be identified. This "negative" diagnosis is of great significance, since it eliminates the need of subjecting a patient to unnecessary treatment or intervention, which could have potential side-effects, or may otherwise put the patient, fetus, or neonate at risk. The data are analyzed to determine if the differences are statistically significant.

The results detailed in the Examples below present proteomic profiles characteristics of intra-amniotic infection (IAI) that differ from the normal proteomic profile of cervical-vaginal fluid (CVF) in a statistically significant manner. In addition, the Examples present expression markers and unique expression signatures characteristic of IAI.

A particularly advantageous biological fluid for performing the non-invasive diagnostic methods of the present invention is the cervical-vaginal fluid (CVF). CVF is a complex biological fluid consisting of water, electrolytes, low-molecular-weight organic compounds (glucose, amino acids, and lipids), cells (leukocytes, lymphocytes, and epithelial cells), and a multitude of proteins and proteolytic enzymes that are predominantly synthesized by the endocervix (Blandau et al., The Biology of the Cervix. University of Chicago Press: Chicago, 1973; p xi, 450p. CVF also contains secretions from vaginal cells, which include mucins, defensins, complement factors, immunogloblins, lactoferrin, and collectins (Blandau et al., supra). CVF flows over and lubricates the entire female reproductive tract, including the vagina, cervical, and uterine areas. CVF forms the first line of defense against external pathogens, signals fertility, and aids insemination, pregnancy, and labor (Blandau et al., supra; Bigelow, J. L. et al., Hum Reprod 2004, 19, (4), 889-92). CVF also contains flora such as *Lactobacilli crispatus* and *Lactobacilli vaginalis*. Secretions from this flora impart a low pH to the CVF, which enhances its anti-pathogen activity (Blandau et al., supra). Any imbalance in the vaginal flora or invasion of external flora results in bacterial vaginosis. In response to bacterial vaginosis, the secretion of several cytokines such as IL-1a, IL-1f3, IL-10, IL-8 and TNF-ct into the CVF by the cervical and vaginal endoepithelia changes (Mattsby-Baltzer, I et al., Acta Obstet Gynecol Scand 1998, 77, (7), 701-6; Eschenbach, D. A. et al., J Clin Microbiol 1989, 27, (2), 251-6). Failure to curb bacterial vaginosis has been positively correlated with cervical cancer (Mikamo, H et al., J Infect Chemother 1999, 5, (2), 82-85), pelvic inflammatory disease (Ness, R. B. et al., Am J Epidemiol 2005, 162, (6), 585-90.), endometritis (Haggerty, C. L. et al., Clin Infect Dis 2004, 39, (7), 990-5; Morris, M. et al., Bjog 2001, 108, (5), 439-50), and tubal infertility (Morris et al., supra). Bacterial vaginosis in pregnant women has been correlated with an increased risk of preterm labor and preterm birth (Gravett, M. G. et al., Jama 1986, 256, (14), 1899-903).

The cytokines and other defense molecules present in CVF also play an important role in infection, replication, and proliferation of sexually transmitted immune-deficiency viruses such as HIV and Herpes Simplex Virus (HSV) in the vagina (Poli, G. et al., AIDS Res Hum Retroviruses 1992, 8, (2), 191-7; Zara, F. et al., Sex Transm Infect 2004, 80, (2), 108-12; John, M. et al., J Infect Dis 2005, 192, (10), 1731-40). Analysis of the cationic polypeptide fraction of the CVF has identified 20 polypeptides that contribute to anti-HIV activity (Venkataraman, N. et al., J Immunol 2005, 175, (11), 7560-7). Previous studies have also identified a role for CVF in the trapping of HIV virions, thus preventing infection (Maher, D. et al., Proc Natl Acad Sci USA 2005, 102, (32), 11504-9; Quinones-Mateu, M. E et al., Aids 2003, 17, (16), F39-48). Recent studies have detected a correlation between several immune-response molecules in CVF and the incidence of subclinical premature rupture of membranes (PROM), which leads to preterm birth (Helmig, B. R. et al., J Matern Fetal Neonatal Med 2002, 12, (4), 237-46; Ogino, M. et al., J Obstet Gynaecol Res 2005, 31, (5), 421-6). During pregnancy, CVF could contain amniotic fluid (AF) derived from the uterus, either due to the disruption or parallel secretions of the chorionic-decidual interface. This "leakage" of AF into CVF provides the basis for the current non-invasive diagnosis for the presence of the fetal fibronectin, which has been used to predict preterm birth in women (Swamy, G. K. et al., J Reprod Med 2005, 50, (11), 851-6).

CVF is an important potential diagnostic site to monitor maternal and fetal health in pregnant women due to its minimally invasive collection method compared to AF, i.e., amniocentesis. The biomarkers and groups or combinations of biomarkers identified herein provide a valuable diagnostic tool in the reliable detection of intra-amniotic infection in a pregnant subject.

Statistical methods for comparing proteomic profiles are well known in the art. For example, the protein expression levels for a series of biomarkers can be quantitated by immunoassay. The presence or absence of a characteristic expression signature or the substantial identity of two profiles can be determined by matching the proteomic profile (pattern) of a test sample with the proteomic profile (pattern) of a reference or normal sample, with an appropriate algorithm. A statistical method for analyzing proteomic patterns is disclosed, for example, in Petricoin III, et al., The Lancet 359:572-77 (2002).; Issaq et al., Biochem Biophys Commun 292:587-92 (2002); Ball et al., Bioinformatics 18:395-404 (2002); and Li et al., Clinical Chemistry Journal, 48:1296-1304 (2002).

(B) The present invention provides an early and reliable, non-invasive method for the diagnosis of the intra-amniotic infection by proteomic analysis of biological fluids, such as, for example, cervical-vaginal fluid (CVF), amniotic fluid, serum, plasma, urine, cerebrospinal fluid, breast milk, mucus, or saliva. In one embodiment, the invention provides an early and reliable, non-invasive method for the diagnosis of the intra-amniotic infection by immunoassay. In one embodiment, the invention provides an early and reliable, non-invasive method for the diagnosis of the intra-amniotic infection by proteomic analysis of CVF.

By way of non-limiting example, the present invention provides methods for the diagnosis of intra-amniotic infection in a pregnant female subject comprising testing in a maternal cervical vaginal fluid sample obtained from said subject the abundance of at least α-fetoprotein, IL-6 and IGFBP1. Diagnosis of intra-amniotic infection based on the statistically significant difference in abundance of these proteins in patients specimens that are defined as positive for IAI versus control specimens that do not have IAI.

As noted above, in the context of the present invention the term "proteomic profile" is used to refer to a representation of the expression pattern of a plurality of proteins in a biological sample, e.g. a biological fluid at a given time. The proteomic profile can, for example, be represented as a mass spectrum, but other representations based on any physicochemical or biochemical properties of the proteins are also included. Although it is possible to identify and sequence all or some of the proteins present in the proteome of a biological fluid, this is not necessary for the diagnostic use of the proteomic profiles generated in accordance with the present invention. Diagnosis of a particular disease can be based on characteristic differences (unique expression signatures) between a normal proteomic profile, and proteomic profile of the same biological fluid obtained under the same circumstances, when the disease or pathologic condition to be diagnosed is present. The unique expression signature can be any unique feature or motif within the proteomic profile of a test or reference biological sample that differs from the proteomic profile of a corresponding normal biological sample obtained from the same type of source, in a statistically significant manner. For example, if the proteomic profile is presented in the form of a mass spectrum, the unique expression signature is typically a peak or a combination of peaks that differ, qualitatively or quantitatively, from the mass spectrum of a corresponding normal sample. Thus, the appearance of a new peak or a combination of new peaks in the mass spectrum, or any statistically significant change in the amplitude or shape of an existing peak or combination of existing peaks, or the disappearance of an existing peak, in the mass spectrum can be considered a unique expression signature. When the proteomic profile of the test sample obtained from a mammalian subject is compared with the proteomic profile of a reference sample comprising a unique expression signature characteristic of a pathologic maternal or fetal condition, the mammalian subject is diagnosed with such pathologic condition if it shares the unique expression signature with the reference sample.

A particular pathologic maternal/fetal condition can be diagnosed by comparing the proteomic profile of a biological fluid obtained from the subject to be diagnosed with the proteomic profile of a normal biological fluid of the same kind, obtained and treated the same manner. If the proteomic profile of the test sample is essentially the same as the proteomic profile of the normal sample, the subject is considered to be free of the subject pathologic maternal/fetal condition. If the proteomic profile of the test sample shows a unique expression signature relative to the proteomic profile of the normal sample, the subject is diagnosed with the maternal/fetal condition in question.

Alternatively or in addition, the proteomic profile of the test sample may be compared with the proteomic profile of a reference sample, obtained from a biological fluid of a subject independently diagnosed with the pathologic maternal/fetal condition in question. In this case, the subject is diagnosed with the pathologic condition if the proteomic profile of the test sample shares at least one feature, or a combination of features representing a unique expression signature, with the proteomic profile of the reference sample.

In the methods of the present invention the proteomic profile of a normal biological sample plays an important diagnostic role. As discussed above, if the proteomic profile of the test sample is essentially the same as the proteomic profile of the normal biological sample, the patient is diagnosed as being free of the pathologic maternal/fetal condition to be identified. This "negative" diagnosis is of great significance, since it eliminates the need of subjecting a patient to unnecessary treatment or intervention, which could have potential side-effects, or may otherwise put the patient, fetus, or neonate at risk. The data are analyzed to determine if the differences are statistically significant.

The sensitivity of the diagnostic methods of the present invention can be enhanced by removing the proteins found both in normal and diseased proteome at essentially the same expression levels (common proteins, such as albumin and immunoglobulins) prior to analysis using conventional protein separation methods. The removal of such common proteins, which are not part of the unique expression signature, results in improved sensitivity and diagnostic accuracy. Alternatively or in addition, the expression signatures of the common proteins can be eliminated (or signals can be removed) during computerized analysis of the results, typically using spectral select algorithms, that are machine oriented, to make diagnostic calls.

The results detailed in the Examples below present proteomic profiles characteristics of intra-amniotic infection (IAI) that differ from the normal proteomic profile of cervical-vaginal fluid (CVF) in a statistically significant manner. In addition, the Examples present expression markers and unique expression signatures characteristic of IAI.

A particularly advantageous biological fluid for performing the non-invasive diagnostic methods of the present invention is the cervical-vaginal fluid (CVF). CVF is a complex biological fluid consisting of water, electrolytes, low-molecular-weight organic compounds (glucose, amino acids, and lipids), cells (leukocytes, lymphocytes, and epithelial cells), and a multitude of proteins and proteolytic enzymes that are predominantly synthesized by the endocervix (Blandau et al., The Biology of the cervix. University of Chicago Press: Chicago, 1973; p xi, 450p. CVF also contains secretions from vaginal cells, which include mucins, defensins, complement factors, immunogloblins, lactoferrin, and collectins (Blandau et al., supra). CVF flows over and lubricates the entire female reproductive tract, including the vagina, cervical, and uterine areas. CVF forms the first line of defense against external pathogens, signals fertility, and aids insemination, pregnancy, and labor (Blandau et al., supra; Bigelow, J. L. et al., Hum Reprod 2004, 19, (4), 889-92). CVF also contains flora such as *Lactobacilli crispatus* and *Lactobacilli vaginalis*. Secretions from this flora impart a low pH to the CVF, which enhances its anti-pathogen activity (Blandau et al., supra). Any imbalance in the vaginal flora or invasion of external flora results in bacterial vaginosis. In response to bacterial vaginosis, the secretion of several cytokines such as IL-1α, IL-1β, IL-10, IL-6 and TNF-α into the CVF by the cervical and vaginal endoepithelia changes (Mattsby-Baltzer, I et al., Acta Obstet Gynecol Scand 1998, 77, (7), 701-6; Eschenbach, D. A. et al., J Clin Microbiol 1989, 27, (2), 251-6). Failure to curb bacterial vaginosis has been positively correlated with cervical cancer (Mikamo, H et al., J Infect Chemother 1999, 5, (2), 82-85), pelvic inflammatory disease (Ness, R. B. et al., Am J Epidemiol 2005, 162, (6), 585-90.), endometritis (Haggerty, C. L. et al., Clin Infect Dis 2004, 39, (7), 990-5; Morris, M. et al., Bjog 2001, 108, (5), 439-50), and tubal infertility (Morris et al., supra). Bacterial vaginosis in pregnant women has been correlated with an increased risk of preterm labor and preterm birth (Gravett, M. G. et al., Jama 1986, 256, (14), 1899-903).

The cytokines and other defense molecules present in CVF also play an important role in infection, replication, and proliferation of sexually transmitted immune-deficiency viruses such as HIV and Herpes Simplex Virus (HSV) in the vagina (Poli, G. et al., AIDS Res Hum Retroviruses 1992, 8, (2), 191-7; Zara, F. et al., Sex Transm Infect 2004, 80, (2), 108-12; John, M. et al., J Infect Dis 2005, 192, (10), 1731-40). Analysis of the cationic polypeptide fraction of the CVF has identified 20 polypeptides that contribute to anti-HIV activity (Venkataraman, N. et al., J Immunol 2005, 175, (11), 7560-7). Previous studies have also identified a role for CVF in the trapping of HIV virions, thus preventing infection (Maher, D. et al., Proc Natl Acad Sci USA 2005, 102, (32), 11504-9; Quinones-Mateu, M. E et al., Aids 2003, 17, (16), F39-48). Recent studies have detected a correlation between several immune-response molecules in CVF and the incidence of subclinical premature rupture of membranes (PROM), which leads to preterm birth (Helmig, B. R. et al., J Matern Fetal Neonatal Med 2002, 12, (4), 237-46; Ogino, M. et al., J Obstet Gynaecol Res 2005, 31, (5), 421-6). During pregnancy, CVF could contain amniotic fluid (AF) derived from the uterus, either due to the disruption or parallel secretions of the chorionic-decidual interface. This "leakage" of AF into CVF provides the basis for the current non-invasive diagnosis for the presence of the fetal fibronectin, which has been used to predict preterm labor in women (Swamy, G. K. et al., J Reprod Med 2005, 50, (11), 851-6).

CVF is an important potential diagnostic site to monitor maternal and fetal health in pregnant women due to its minimally invasive collection method compared to AF, i.e., amniocentesis. The combinations of biomarkers identified herein provides a valuable diagnostic tool in the reliable detection of intra-amniotic infection in a pregnant subject.

Statistical methods for comparing proteomic profiles are well known in the art. For example, in the case of a mass spectrum, the proteomic profile is defined by the peak amplitude values at key mass/charge (M/Z) positions along the horizontal axis of the spectrum. Accordingly, a characteristic proteomic profile can, for example, be characterized by the pattern formed by the combination of spectral amplitudes at given M/Z vales. The presence or absence of a characteristic expression signature, or the substantial identity of two profiles can be determined by matching the proteomic profile (pattern) of a test sample with the proteomic profile (pattern) of a reference or normal sample, with an appropriate algorithm. A statistical method for analyzing proteomic patterns is disclosed, for example, in Petricoin III, et al., The Lancet 359:572-77 (2002).; Issaq et al., Biochem Biophys Commun 292:587-92 (2002); Ball et al., Bioinformatics 18:395-404 (2002); and Li et al., Clinical Chemistry Journal, 48:1296-1304 (2002).

4. Protein Arrays

Both the diagnostic and the screening assays discussed above can be performed using protein arrays. In recent years, protein arrays have gained wide recognition as a powerful means to detect proteins, monitor their expression levels, and investigate protein interactions and functions. They enable high-throughput protein analysis, when large numbers of determinations can be performed simultaneously, using automated means. In the microarray or chip format, that was originally developed for DNA arrays, such determinations can be carried out with minimum use of materials while generating large amounts of data.

Although proteome analysis by 2D gel electrophoresis and mass spectrometry is very effective, it does not always provide the needed high sensitivity and this might miss many proteins that are expressed at low abundance. Protein microarrays, in addition to their high efficiency, provide improved sensitivity.

Protein arrays are formed by immobilizing proteins on a solid surface, such as glass, silicon, plastic micro-wells, nitrocellulose, PVDF membranes, and microbeads, using a variety of covalent and non-covalent attachment chemistries well known in the art. The solid support should be chemically stable before and after the coupling procedure, allow good spot morphology, display minimal nonspecific binding, should not contribute a background in detection systems, and should be compatible with different detection systems.

In general, protein microarrays use the same detection methods commonly used for the reading of DNA arrays. Similarly, the same instrumentation as used for reading DNA microarrays is applicable to protein arrays.

Thus, capture arrays (e.g. antibody arrays) can be probed with fluorescently labelled proteins from two different sources, such as normal and diseased biological fluids. In this case, the readout is based on the change in the fluorescent signal as a reflection of changes in the expression level of a target protein. Alternative readouts include, without limitation, fluorescence resonance energy transfer, surface plasmon resonance, rolling circle DNA amplification, resonance light scattering, enzyme reactions and atomic force microscopy.

For further details, see, for example, Zhou H, et al., Trends Biotechnol. 19:S34-9 (2001); Zhu et al., Current Opin. Chem. Biol. 5:40-45-(2001); Wilson and Nock, Angew Chem Int Ed Engl 42:494-500 (2003); and Schweitzer and Kingsmore, Curr Opin Biotechnol 13:14-9 (2002). Biomolecule arrays are also disclosed in U.S. Pat. No. 6,406,921, issued Jun. 18, 2002, the entire disclosure of which is hereby expressly incorporated by reference.

5. Immunoassays

The diagnostic assays of the present invention can also be performed in the form of various immunoassay formats, which are well known in the art. One embodiment of the invention includes methods for diagnosing intra-amniotic infection in an individual, comprising the steps of obtaining a body fluid, e.g., cervical-vaginal fluid, from an individual; measuring an amount of one or more proteins described herein in the body fluid using immunoassay systems described herein; and comparing the amount of the one or more proteins described herein in the body fluid to a reference level of the one or more proteins described herein in healthy individuals without the condition, wherein an elevated amount of the one or more proteins described herein above the reference level indicates the individual has intra-amniotic infection.

In one embodiment, a one-step assay (simultaneous incubation of sample plus detection antibody) is useful. In another embodiment, a two-step assay (sequential incubation of sample and the detection antibody) is useful. A two-step assay is preferable in the case where other protein molecules could compete for binding to the detection antibody. In homogeneous immunoassays, both the immunological reaction between an antigen and an antibody and the detection are carried out in a homogeneous reaction. Heterogeneous immunoassays include at least one separation step, which allows the differentiation of reaction products from unreacted reagents.

In an embodiment of an immunoassay referred to as immunometric, "two-site" or "sandwich" immunoassay, the analyte is bound to or sandwiched between two antibodies that bind to different epitopes on the analyte. Representative examples of such immunoassays include enzyme immunoassays or enzyme-linked immunosorbent assays (EIA or ELISA), immunoradiometric assays (IRMA), fluorescent immunoassays, lateral flow assays, diffusion immunoassays, immunoprecipitation assays, and magnetic separation assays (MSA). In one such assay, a first antibody, which is described as the "capture" antibody, is bound to a solid support, such as a protein coupling or protein binding surface, colloidal metal particles, iron oxide particles, or polymeric beads. One example of a polymeric bead is a latex particle. In such an embodiment, the capture antibody is bound to or coated on a solid support using procedures known in the art. Alternatively, the capture antibody is coupled with a ligand that is recognized by an additional antibody that is bound to or coated on a solid support. Binding of the capture antibody to the additional antibody via the ligand then indirectly immobilizes the capture antibody on the solid support. An example of such a ligand is fluorescein.

The second antibody, which is described as the "detection" antibody, is coupled or conjugated with a label using procedures known in the art. Examples of suitable labels for this purpose include a chemiluminescent agent, a colorimetric agent, an energy transfer agent, an enzyme, a substrate of an enzymatic reaction, a fluorescent agent and a radioisotope. In one embodiment, the label includes a first protein such as biotin coupled with the second antibody, and a second protein such as streptavidin that is coupled with an enzyme. The second protein binds to the first protein. The enzyme produces a detectable signal when provided with substrate(s), so that the amount of signal measured corresponds to the amount of second antibody that is bound to the analyte. Examples of enzymes include, without limitation, alkaline phosphatase, amylase, luciferase, catalase, beta-galactosidase, glucose oxidase, glucose-6-phosphate dehydrogenase, hexokinase, horseradish peroxidase, lactamase, urease and malate dehydrogenase. Suitable substrates include, without limitation, TMB (3,3',5,5'-tetramethyl benzidine, OPD (o-phenylene diamine), and ABTS (2,2'-azino-bis(3-ethylbenzthiazoline-6-sulfonic acid).

In the "sandwich" format the antigen being assayed is held between two different antibodies. In this method, a solid surface is first coated with a solid phase antibody. The test sample, containing the antigen (i.e. a diagnostic protein), or a composition containing the antigen, being measured, is then added and the antigen is allowed to react with the bound antibody. Any unbound antigen is washed away. A known amount of enzyme-labeled antibody is then allowed to react with the bound antigen. Any excess unbound enzyme-linked antibody is washed away after the reaction. The substrate for the enzyme used in the assay is then added and the reaction between the substrate and the enzyme produces a color change. The amount of visual color change is a direct measurement of specific enzyme-conjugated bound antibody, and consequently the antigen present in the sample tested.

ELISA can also be used as a competitive assay. In the competitive assay format, the test specimen containing the antigen to be determined is mixed with a precise amount of enzyme-labeled antigen and both compete for binding to an anti-antigen antibody attached to a solid surface. Excess free enzyme-labeled antigen is washed off before the substrate for the enzyme is added. The amount of color intensity resulting from the enzyme-substrate interaction is a measure of the amount of antigen in the sample tested. Homogeneous immunoassays include, for example, the Enzyme Multiplied Immunoassay Technique (EMIT®), which typically includes a biological sample comprising the compound or compounds to be measured, enzyme-labeled molecules of the compound(s) to be measured, specific antibody or antibodies binding the compound(s) to be measured, and a specific enzyme chromogenic substrate. In a typical EMIT excess of specific antibodies is added to a biological sample. If the biological sample contains the proteins to be detected, such proteins bind to the antibodies. A measured amount of the corresponding enzyme-labeled proteins is then added to the mixture. Antibody binding sites not occupied by molecules of the protein in the sample are occupied with molecules of the added enzyme-labeled protein. As a result, enzyme activity is reduced because only free enzyme-labeled protein can act on the substrate. The amount of substrate converted from a colorless to a colored form determines the amount of free enzyme left in the mixture. A high concentration of the protein to be detected in the sample causes higher absorbance readings. Less protein in the sample results in less enzyme activity and consequently lower absorbance readings. Inactivation of the enzyme label when the Ag-enzyme complex is Ab-bound makes the EMIT a unique system, enabling the test to be performed without a separation of bound from unbound compounds as is necessary with other immunoassay methods.

Antibodies useful in the various embodiments of the systems and methods described herein include commercially available antibodies and antibody fragments, as well as any novel antibodies generated to bind a suitable epitope on the designated target protein. In all embodiments, the antibodies to be used in accordance with the present invention must bind the one or more specific isoforms of the biomarkers described herein which are present in cervical-vaginal fluid. The antibodies used in various embodiments exemplified herein are monoclonal or polyclonal in nature. Other antibodies and antibody fragments, such as recombinant antibodies, chimeric antibodies, humanized antibodies, antibody fragments such as Fab or Fv fragments, as well as fragments selected by screening phage display libraries, and the like are also useful in the compositions and methods described herein.

Methods for preparation of monoclonal as well as polyclonal antibodies are now well established (Harlow E. et al., 1988. Antibodies. New York: Cold Spring Harbour Laboratory). In one embodiment, antibodies are raised against recombinant human LBP, synthetic fragments thereof, or LBP, such as may be purified from human sera. Polyclonal antibodies are raised in various species including but not limited to mouse, rat, rabbit, goat, sheep, donkey and horse, using standard immunization and bleeding procedures. Animal bleeds with high titers are fractionated by routine selective salt-out procedures, such as precipitation with ammonium sulfate and specific immunoglobulin fractions being separated by successive affinity chromatography on Protein-A-Sepharose and leptin-Sepharose columns, according to standard methods. The purified polyclonal as well as monoclonal antibodies are then characterised for specificity and lack of cross-reactivity with related molecules. Such characterization is performed by standard methods using proteins, for example LBP, labeled with a tracer such as a radioisotope or biotin in competition with increasing levels of unlabeled potential cross-reactants for antibody binding. In some embodiments, further purification is required to obtain highly specific antibody fractions or for selection of higher affinity antibody fractions from a polyclonal pool. In the case of monoclonal antibodies, care is taken to select antibodies with good binding characteristics and specificity not only for the immunogen, but also for the native circulating molecules, particularly when a recombinant molecule or peptide antigen is used for immunization. Cross-reactivity studies are further evaluated by other standard methods such as the well-established sodium dodecyl sulphate-polyacrylamide gel electrophoresis (SDS-PAGE) and Western immunoblot methods under reducing and non-reducing conditions. Evaluation of protein immunoreactivity detected in serum samples fractionated by high performance liquid chromatography (HPLC) is also used to roughly define the molecular weight profile of the protein detected (Gravett M G, et al., JAMA 2004; 292:462-469; Khosravi M J et al., Clin Biochem 1995; 28:407-414).

Monoclonal antibodies are prepared according to well established standard laboratory procedures ("Practice and Theory of Enzyme Immunoassays" by P. Tijssen (In Laboratory Techniques in Biochemistry and Molecular Biology, Eds: R. H. Burdon and P. H. van Kinppenberg; Elsevier Publishers Biomedical Division, 1985)), which are based on the original technique of Kohler and Milstein (Kohler G., Milstein C. Nature 256:495, 1975). This technique is performed by removing spleen cells from immunized animals and immortalizing the antibody producing cells by fusion with myeloma cells or by Epstein-Barr virus transformation, and then screening for clones expressing the desired antibody, although other techniques known in the art are also used. Antibodies are also produced by other approaches known to those skilled in the art, including but not limited to immunization with specific DNA.

For use in the immunoassays described herein, antibodies are purified using standard antibody purification schemes. In various embodiments, both monoclonal and polyclonal antibodies are purified by affinity chromatography over Protein-A columns. Alternatively, the antibodies are purified by affinity chromatography over a gel column containing immobilized antigen protein using standard methods.

Another consideration for selection of the appropriate antibody for use in the systems and methods described herein is the ability of the capture antibody and the detection antibody to bind simultaneously to a given protein molecule. In one embodiment involving an MIP1b, for example, the anti-MIP1b binding site of the capture antibody is different from the epitope to which the detection antibody binds, thus allowing for simultaneous binding of the capture and detection antibodies and detection of the specific biomarker. In the case of significant overlap of epitopes and a resulting poor binding response, it is within the skill of one in the art to select a different antibody to the biomarker as the capture or detection antibody. In some embodiments an antibody binding site is not entirely available on the surface of the protein, for example where the protein is mainly present in the sample in a complex with one or more other proteins, and is less accessible for binding to the capture or detection antibodies. In such a circumstance, techniques known in the art are used to expose the antibody binding sites, such as partial protein denaturation or buffer modification.

As known in the art, the capture antibody is coupled with or linked to various solid phase supports using standard non-covalent or covalent binding methods, depending on the required analytical and/or solid-phase separation requirements. The solid-support is in the form of test tubes, beads, microparticles, filter paper, membranes, glass filters, magnetic particles, glass or silicon chips or other materials and approaches known to those skilled in the art. The use of microparticles, particularly magnetizable particles, that have been directly coated with the antibody (magnetic particles-capture antibody) or particles that have been labeled with a universal binder (e.g., avidin or anti-species antibody) is useful for significantly shortening the assay incubation time. These along with other alternative approaches known in the art allow for assay completion within minutes without limiting the required sensitivity. The use of magnetizable particles or similar approaches allow for convenient automation of the technology on the widely available immunoanalyzers.

The detection antibody used for detection of the protein fragment is either directly coupled with a reporter molecule, or detected indirectly by a secondary detection system. The latter is based on several different principles known in the art, including antibody recognition by a labeled anti-species antibody and other forms of immunological or non-immunological bridging and signal amplification detection systems (e.g., the biotin-streptavidin technology). The signal amplification approach is used to significantly increase the assay sensitivity and low level reproducibility and performance. The label used for direct or indirect antibody coupling is any detectable reporter molecule. Examples of suitable labels are those widely used in the field of immunological and non-immunological detection systems, such as fluorophores, luminescent labels, metal complexes and radioactive labels, as well as moieties that could be detected by other suitable reagents such as enzymes, or various combinations of direct or indirect labels such as enzymes with luminogenic substrates.

In various embodiments of the methods of the invention, any sample and antibody volumes and incubation times are within the skill of one in the art to alter. These methods and systems include common modifications used in conventional immunoassays, and any modification known to those skilled in the art. In various embodiments, the assay design is homogeneous or heterogeneous, depending on the particular application of the assay and the need for speed, sensitivity, accuracy and convenience.

In addition to the immunoassays described above, other immunoassays (e.g., Ouchterlony plates or Western blots may be performed on protein gels or protein spots on filters) are known in the art and may find use as diagnostics.

Another aspect of the present invention concerns an immunoassay kit. In one embodiment, the immunoassay kit comprises antibodies and reagents for the detection of two or more of the proteins described herein. In one aspect, the invention includes a sandwich immunoassay kit comprising a capture antibody and a detector antibody. The capture antibody and detector antibody can be monoclonal or polyclonal. In another aspect, the invention includes a diagnostic kit comprising lateral flow devices, such as immunochromatographic strip (ICS) tests, using immunoflowchromatography. The lateral flow devices employ lateral flow assay techniques as generally described in U.S. Pat. Nos. 4,943,522; 4,861,711; 4,857,453; 4,855,240; 4,775,636; 4,703,017; 4,361,537; 4,235,601; 4,168,146; 4,094,647, the entire contents of each of which is incorporated by reference. In yet another aspect, the immunoassay kit may comprise, for example, in separate containers (a) monoclonal antibodies having binding specificity for the polypeptides used in the diagnosis of a particular maternal/fetal condition, such as neonatal sepsis; (b) and anti-antibody immunoglobulins. This immunoassay kit may be utilized for the practice of the various methods provided herein. The monoclonal antibodies and the anti-antibody immunoglobulins may be provided in an amount of about 0.001 mg to about 100 grams, and more preferably about 0.01 mg to about 1 gram. The anti-antibody immunoglobulin may be a polyclonal immunoglobulin, protein A or protein G or functional fragments thereof, which may be labeled prior to use by methods known in the art. The diagnostic kit may further include where necessary agents for reducing background interference in a test, agents for increasing signal, software and algorithms for combining and interpolating marker values to produce a prediction of clinical outcome of interest, apparatus for conducting a test, calibration curves and charts, standardization curves and charts, and the like. The test kit may be packaged in any suitable manner, typically with all elements in a single container along with a sheet of printed instructions for carrying out the test.

6. Diagnostic and Treatment Methods

The diagnostic methods of the present invention are valuable tools for practicing physicians to make quick treatment decisions, which are often critical for the survival of the infant and/or mother. Thus, for example, if a pregnant woman shows symptoms of pre-term labor, it is important to perform a diagnostic test to determine if intra-amniotic infection is present. If the quick and non-invasive diagnostic test herein confirms the presence of intra-amniotic infection, the physician needs to take immediate steps to improve the chances of the survival of the pre-term infant and limit the risks to the mother's health. There are no non-invasive tests for intraamniotic infection available today.

If the test for intra-amniotic infection is negative, the question remains if a pre-term delivery is still to be expected. Currently, sometimes a single-marker fetal fibronectin (fFN) test is used for this purpose. The absence of fFN in the CVF of the pregnant patient is a good indicator that the pregnancy will continue for at least two additional weeks. However, based on the presence of fFN (positive test), it is not possible to reliably predict whether pre-term birth in likely to take place. The multi-marker diagnostic tests of the present invention provide reliable predictors of the likelihood of pre-term delivery both in the case of negative and positive test results.

Alternatively, if the patient shows symptoms of pre-term delivery and a diagnostic test (either a test herein or any other test used in clinical practice) is used to assess the likelihood of pre-term delivery, a test for intra-amniotic infection can be performed as a follow-up, to provide information concerning the presence or absence of intraamniotic infection and enable the physician to make better treatment decisions.

Following the measurement or obtainment of the expression levels of the proteins identified herein, the assay results, findings, diagnoses, predictions and/or treatment recommendations are typically recorded and communicated to technicians, physicians and/or patients, for example. In certain embodiments, computers will be used to communicate such information to interested parties, such as, patients and/or the attending physicians. In some embodiments, the assays will be performed or the assay results analyzed in a country or jurisdiction which differs from the country or jurisdiction to which the results or diagnoses are communicated.

In a preferred embodiment, a diagnosis, prediction and/or treatment recommendation based on the expression level in a test subject of one or more of the biomarkers herein is communicated to the subject as soon as possible after the assay is completed and the diagnosis and/or prediction is generated. In certain embodiments, the diagnosis, prediction and/or treatment recommendation is further based on signs and symptoms presented by the subject. In one embodiment, signs and symptoms indicating IAI include, but are not limited to, maternal fever ($\geq 37.8°$ C.), maternal leukocytosis ($\geq 15,000/mm^3$), maternal or fetal tachycardia, uterine tenderness, or foul-smelling amniotic fluid. Other signs and symptoms indicating IAI are known in the art. The one or more biomarkers identified and quantified in the methods described herein can be contained in one or more panels. The number of biomarkers comprising a panel can include 1 biomarker, 2 biomarkers, 3 biomarkers, 4 biomarkers, 5 biomarkers, 6 biomarkers, 7 biomarkers, 8 biomarkers, 9 biomarkers, 10 biomarkers, 11 biomarkers, 12 biomarkers, 13 biomarkers, 14 biomarkers, 15 biomarkers, 16 biomarkers, 17 biomarkers, 18 biomarkers, 19 biomarkers, 20 biomarkers, etc.

In a preferred embodiment, the invention concerns an intraamniotic infection test (ProteoGenix intraamniotic infection test (PG-IAI)), which is an immunochromatographic test that measures α-fetoprotein, Interleukin-6 (IL-6) and Insulin Growth Factor Binding Protein-1 (IGFBP-1) concentrations in cervical vaginal fluid (CVF). The test is particularly useful as an aid in assessing the risk of IAI in pregnant women with idiopathic preterm labor, intact membranes and sampled between 22 weeks 0 days and 36 weeks 6 days, and can be used to prioritize patient management for those suspected of IAI.

In a particular embodiment, the test is housed in a lateral flow cartridge, and PG-IAI biomarker signal intensities are measured using a lateral flow reader. The CVF is collected using a non-invasive CVF swab using a swab collection kit.

Data from current clinical/analytical studies using an ELISA platform were used to approximate test performance for the lateral flow device. The best model used mass concentrations of two CVF biomarkers, α-fetoprotein and IL-6. The additional CVF biomarker, IGFBP1, has been identified that serves as a gatekeeper for the two biomarker risk assessment. While IGFBP1 may not be diagnostic for IAI on its own, it rejects 29% of IAI false positive patient results and greatly improves specificity of the diagnostic test.

The results and/or related information may be communicated to the subject by the subject's treating physician. Alternatively, the results may be communicated directly to a test subject by any means of communication, including writing, such as by providing a written report, electronic forms of communication, such as email, or telephone. Communication may be facilitated by use of a computer, such as in case of email communications. In certain embodiments, the communication containing results of a diagnostic test and/or conclusions drawn from and/or treatment recommendations based on the test, may be generated and delivered automatically to the subject using a combination of computer hardware and software which will be familiar to artisans skilled in telecommunications. One example of a healthcare-oriented communications system is described in U.S. Pat. No. 6,283,761; however, the present invention is not limited to methods which utilize this particular communications system. In certain embodiments of the methods of the invention, all or some of the method steps, including the assaying of samples, diagnosing of diseases, and communicating of assay results or diagnoses, may be carried out in diverse (e.g., foreign) jurisdictions.

To facilitate diagnosis, the reference and/or subject biomarker profiles or expression level of one or more of the biomarkers presented herein of the present invention can be displayed on a display device, contained electronically, or in a machine-readable medium, such as but not limited to, analog tapes like those readable by a VCR, CD-ROM, DVD-ROM, USB flash media, e.g., flash drive, among others. Such machine-readable media can also contain additional test results, such as, without limitation, measurements of clinical parameters and traditional laboratory risk factors. Alternatively or additionally, the machine-readable media can also comprise subject information such as medical history and any relevant family history.

Microbiology and Treatment:

IAI is frequently a polymicrobial infection, involving eubacteria, *mycoplasma* sp. and fungi. The most frequent microorganisms recovered by culture or 16S rDNA PCR from amniotic fluid in IAI included *Gardnerella vaginalis, Bacteroides bivus. Fusobacterium nucleatum, Peptostroptococcus* sp., *Provotella bivus*, other Gram-negative anaerobes, *Candida*, as well as the genital *mycoplasmas Mycoplasma hominis* and *Ureaplasma urealyticum*. (DiGiulio D B, et al., PLoS ONE 3(8): e3056; Han, Yiping W. et al., J. Clin. Microbiol. 2009 47: 38-47). Targeted antibiotic therapy should be initiated in the intrapartum period, as soon as the diagnosis is confirmed.

All patent and literature references cited in the present specification are hereby incorporated by reference in their entirety.

EXAMPLES

The following example is offered for illustrative purposes only and is not intended to limit the scope of the present invention in any way. One of skill in the art will recognize a variety of parameters that can be altered within the scope of the invention.

Example 1

Identification of Cervical Vaginal Fluid Biomarkers of Intra-Amniotic Infection Using Immunoassays Individual patient specimens were collected from patients presenting in pre-term labor. Matched amniotic fluid specimens were used to classify the patients as presenting with intraamniotic infection (IAI) or without non-IAI based on amniotic fluid culture (aerobic, anaerobic and *Mycoplasma* sp) and the presence or absence of amniotic fluid 16S ribosomal DNA.

Cervical Vaginal Fluid Swab Collection.

Cervical vaginal fluid was collected by swabbing the cervical os with a polyester swab (Puritan, Guilford, Me.), which was then placed into a container with ~1 mL of specimen collection buffer. Specimens were frozen at −70° C. for transport, then thawed, centrifuged for 15 min at 270×g and re-aliquotted for long term storage.

GROalpha:

Dilution of CVF specimens. Cervical vaginal fluid (CVF) specimens were diluted 1:50 in Assay Buffer (2.67 mM KCl, 1.47 mM KH2PO4, 137.93 mM NaCl, 8.06 mM Na2HPO4-7H2O, 0.15% BSA, 0.05% v/v TWEEN®-20, 0.075% v/v PROCLIN® 950 (preservative for diagnostic reagents), pH 7.3+0.3) prior to testing on the QUANTIKINE® Human CXCL1/GROct Immunoassay Kit as described below.

Detection of GROalpha in CVF Specimens.

After dilution, specimens were run as samples on the QUANTIKINE® Human CXCL1/GROct Immunoassay Kit from R&D Systems (Catalog Number DGR00), with some modifications to the manufacturer's instructions. In brief, reagents, controls, and samples were brought to room temperature (RT). The GROct Standard was reconstituted with 5 mL Assay Buffer, generating a 1000 pg/mL solution. This solution was incubated at room temperature for 15 min with gentle agitation. After incubation, 750 µL of the 1000 pg/mL solution was diluted into 750 µL of Assay Buffer, generating a solution of 500 pg/mL. This process was repeated four additional times, generating solutions of 250 pg/mL, 125 pg/mL, 62.5 pg/mL, and 31.25 pg/mL. 50 µL of Assay Diluent RD1U was added to each well. 200 µL of standards were added to appropriate wells in triplicate. 200 µL of controls and samples were added to appropriate wells in duplicate. The wells were covered with an adhesive strip and incubated at RT for 2 hr. The adhesive strip was removed and the wells were washed 3× with 400 μL 1× Wash Buffer with a 1 min incubation between washes using the BioTek ELx50™ plate washer. Any residual liquid was removed by pounding the wells upside down on paper towels. 200 μL of GROct Conjugate was added to each well. The wells were covered with an adhesive strip and incubated at 2-8° C. for 2 hr. The adhesive strip was removed and the wells were washed as before. Any residual liquid was removed as before. 200 μL of Substrate Solution was added to each well. The wells were covered with aluminum foil and incubated at RT for 20 min. 50 μL of Stop Solution was added to each well. The plate was read at 450 nm and 540 nm using the BioTek SYNERGY™ 2 plate reader and the BioTek GEN5™ software.

Quantification of GROalpha in CVF Specimens.

Using the GEN5™ software, four parameter nonlinear regression analysis was performed to generate a standard curve. This standard curve was then used to calculate the concentrations of GROalpha in the CVF specimens run on the immunoassay kit. In order to calculate the final concentrations of GROalpha in the CVF specimens, the calculated concentrations were multiplied by 50 in order to account for the initial specimen dilution. Any specimens that had Delta OD (OD450-OD540) readings lower than the Delta OD reading of the 31.25 pg/mL standard were assigned a concentration of 31.25 pg/mL, which was then multiplied by 50. The data were then analyzed using statistical methods as described below. FIG. 1 depicts boxplots showing natural logarithm value of GROalpha (Assay 1) in IAI infected (n=14) vs. non-infected patients (n=95).

Dilution of CVF Specimens.

Cervical vaginal fluid (CVF) specimens were diluted 1:100 in Calibrator Diluent RD6F prior to testing on the QUANTIKINE® Human IL-6 Immunoassay Kit as described below.

Detection of IL-6 in CVF Specimens.

After dilution, specimens were run as samples on the QUANTIKINE® Human IL-6 Immunoassay Kit from R&D Systems (Catalog Number D6050), with some modifications to the manufacturer's instructions. In brief, reagents, controls, and samples were brought to room temperature (RT). The IL-6 Standard was reconstituted with 5 mL Calibrator Diluent RD6F, generating a 300 pg/mL solution. This solution was incubated at room temperature for 15 min with gentle agitation. After incubation, 333 μL of the 300 pg/mL solution was diluted into 667 μL of Calibrator Diluent RD6F, generating a solution of 100 pg/mL. 500 μL of the 100 pg/mL solution was diluted into 500 μL of Calibrator Diluent RD6F, generating a solution of 50 pg/mL. Two-fold dilutions were repeated four additional times, generating solutions of 25 pg/mL, 12.5 pg/mL, 6.25 pg/mL, and 3.12 pg/mL. 100 μL of Assay Diluent RD1W was added to each well. 100 μL of standards were added to appropriate wells in triplicate. 100 μL of controls and samples were added to appropriate wells in duplicate. The wells were covered with an adhesive strip and incubated at RT for 2 hr. The adhesive strip was removed and the wells were washed 4× with 400 μL 1× Wash Buffer using the BioTek ELx50™ plate washer. Any residual liquid was removed by pounding the wells upside down on paper towels. 200 μL of IL-6 Conjugate was added to each well. The wells were covered with an adhesive strip and incubated at RT for 2 hr. The adhesive strip was removed and the wells were washed as before. Any residual liquid was removed as before. 200 μL of Substrate Solution was added to each well. The wells were covered with aluminum foil and incubated at RT for 20 min. 50 μL of Stop Solution was added to each well. The plate was read at 450 nm and 540 nm using the BioTek SYNERGY™ 2 plate reader and the BioTek GEN5™ software.

Quantitation of IL-6 in CVF Specimens.

Figure 7:
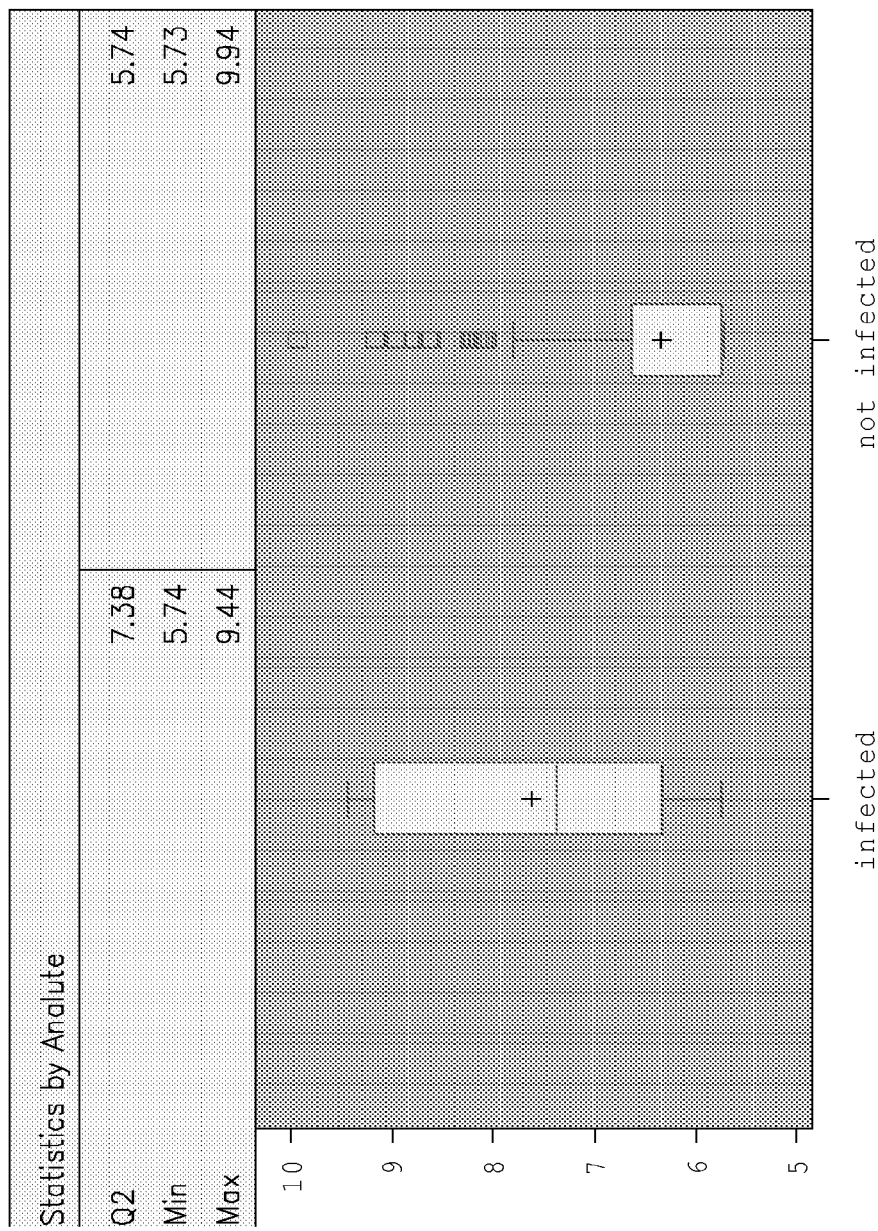
FIG. 7 depicts boxplots showing natural logarithm value of IL-6 in IAI infected (n=14) vs. non-infected patients (n=95).

Using the GEN5™ software, four parameter nonlinear regression analysis was performed to generate a standard curve. This standard curve was then used to calculate the concentrations of IL-6 in the CVF specimens run on the immunoassay kit. In order to calculate the final concentrations of IL-6 in the CVF specimens, the calculated concentrations were multiplied by 100 in order to account for the initial specimen dilution. Any specimens that had Delta OD (OD450-OD540) readings lower than the Delta OD reading of the 3.12 pg/mL standard were assigned a concentration of 3.12 pg/mL, which was then multiplied by 100. Any specimens that had Delta OD readings higher than the Delta OD reading of the 300 pg/mL standard were diluted at higher dilutions and run on the kit again. The data were then analyzed using statistical methods as described below. FIG. 7 depicts boxplots showing natural logarithm value of IL-6 in IAI infected (n=14) vs. non-infected patients (n=95).

LBP: Dilution of CVF Specimens.

Cervical vaginal fluid (CVF) specimens were diluted 1:50 in Assay Buffer (2.67 mM KCl, 1.47 mM KH2PO4, 137.93 mM NaCl, 8.06 mM Na2HPO4-7H2O, 0.15% BSA, 0.05% v/v TWEEN®-20, 0.075% v/v PROCLIN® 950 (preservative for diagnostic reagents), pH 7.3+0.3) prior to testing on the Human LBP ELISA Kit as described below.

Detection of LBP in CVF Specimens.

Figure 8:
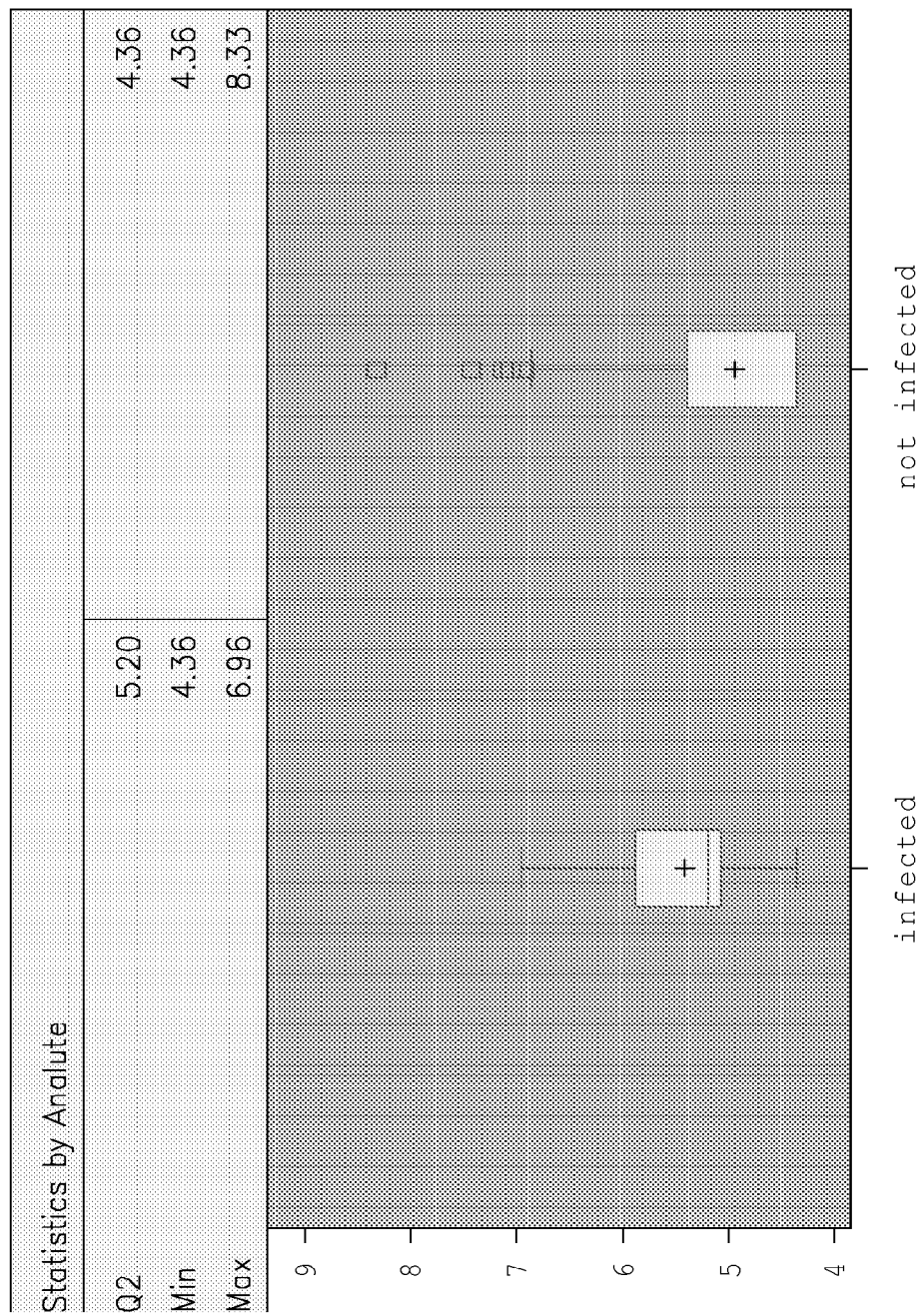
FIG. 8 shows the natural logarithm value of LBP in IAI infected (n=14) vs. non-infected patients (n=95).

After dilution, specimens were run as samples on the Human LBP ELISA Kit from Cell Sciences (Catalog Number CKH113), with some modifications to the manufacturer's instructions. In brief, reagents, controls, and samples were brought to room temperature (RT). The Human LBP Standard was reconstituted with 30 μL distilled water. The reconstituted Human LBP Standard was then diluted into 15704, Assay Buffer, generating a solution of 50 ng/mL. 350 μL of the 50 ng/mL solution was diluted into 350 μL of Assay Buffer, generating a solution of 25 ng/mL. Two-fold dilutions were repeated four additional times, generating solutions of 12.5 ng/mL, 6.25 ng/mL, 3.125 ng/mL, and 1.56 ng/mL. 100 μL of standards were added to appropriate wells in triplicate. 100 μL of controls and samples were added to appropriate wells in duplicate. The wells were covered with an adhesive strip and incubated at RT for 1 hr with shaking. The adhesive strip was removed and the wells were washed 3× with 300 μL Wash Buffer using the BioTek ELx50™ plate washer. Any residual liquid was removed by pounding the wells upside down on paper towels. 100 μL of Detection Antibody was added to each well. The wells were covered with an adhesive strip and incubated at RT for 1 hr with shaking. The adhesive strip was removed and the wells were washed as before. Any residual liquid was removed as before. 100 μL of Substrate Solution was added to each well. The wells were covered with aluminum foil and incubated at RT for 12-15 min. 100 μL of Stop Solution was added to each well. The plate was read at 450 nm and 620 nm using the BioTek SYNERGY™ 2 plate reader and the BioTek GEN5™ software. FIG. 8 depicts the natural logarithm value of LBP in IAI infected (n=14) vs. non-infected patients (n=95).

Quantitation of LBP in CVF Specimens.

Using the GEN5™ software, four parameter nonlinear regression analysis was performed to generate a standard curve. This standard curve was then used to calculate the concentrations of LBP in the CVF specimens run on the immunoassay kit. In order to calculate the final concentrations of LBP in the CVF specimens, the calculated concentrations were multiplied by 50 in order to account for the initial specimen dilution. Any specimens that had Delta OD (OD450-OD620) readings lower than the Delta OD reading of the 1.56 ng/mL standard were assigned a concentration of 1.56 ng/mL, which was then multiplied by 50. Any specimens that had Delta OD readings higher than the Delta OD reading of the 50 ng/mL standard were diluted at higher dilutions and run on the kit again. The data were then analyzed using statistical methods as described below.

A1AG: Dilution of CVF Specimens.

Cervical vaginal fluid (CVF) specimens were diluted 1:200 in PBS with 1% milk prior to testing on the Human Orosomucoid (Alpha-1-Acid Glycoprotein) ELISA Quantitation Kit as described below.

Detection of A1AG in CVF Specimens.

After dilution, specimens were run as samples on the Human Orosomucoid (Alpha-1-Acid Glycoprotein) ELISA Quantitation Kit from GenWay (Catalog Number 40-288-22927F), with some modifications to the manufacturer's instructions. In brief, reagents, controls, and samples were brought to room temperature (RT). The Coating Antibody was diluted to 5 µg/mL in Coating Buffer (0.05M Carbonate-Bicarbonate, pH 9.4). 100 µL of this 5 µg/mL coating solution was added to Immuno LOCKWELL™ modules with a MAXISORP® surface (Nunc, Catalog Number 446469). The wells were incubated at RT for 1 hr and were then washed 3× with 300 µL Wash Solution (50 mM Tris-HCl, 0.14M NaCl, 0.05% TWEEN® 20) using the BioTek ELx50™ plate washer. Any residual liquid was removed by pounding the wells upside down on paper towels. 200 µL of PBS with 1% milk was added to each well and the wells were incubated at RT for 1 hr. The wells were then washed as before and any residual liquid was removed as before. The Calibrator was diluted to 250 ng/mL in PBS with 1% milk. 400 µL of the 250 ng/mL solution was then diluted into 400 µL of PBS with 1% milk, generating a solution of 125 ng/mL. Two-fold dilutions were repeated five additional times, generating solutions of 62.5 ng/mL, 31.25 ng/mL, 15.625 ng/mL, 7.8125 ng/mL, and 3.90625 ng/mL. 100 µL of standards were added to appropriate wells in triplicate. 100 µL of controls and samples were added to appropriate wells in duplicate. The wells were covered with an adhesive strip and incubated at RT for 1 hr. The adhesive strip was removed and the wells were washed 5× with 300 µL Wash Solution using the BioTek ELx50™ plate washer. Any residual liquid was removed as before. The HRP Conjugate was diluted to 480 ng/mL in PBS with 1% milk. 100 µL of diluted HRP Conjugate was then added to each well. The wells were covered with an adhesive strip and incubated at RT for 1 hr. The adhesive strip was removed and the wells were washed as before.

Figure 6:
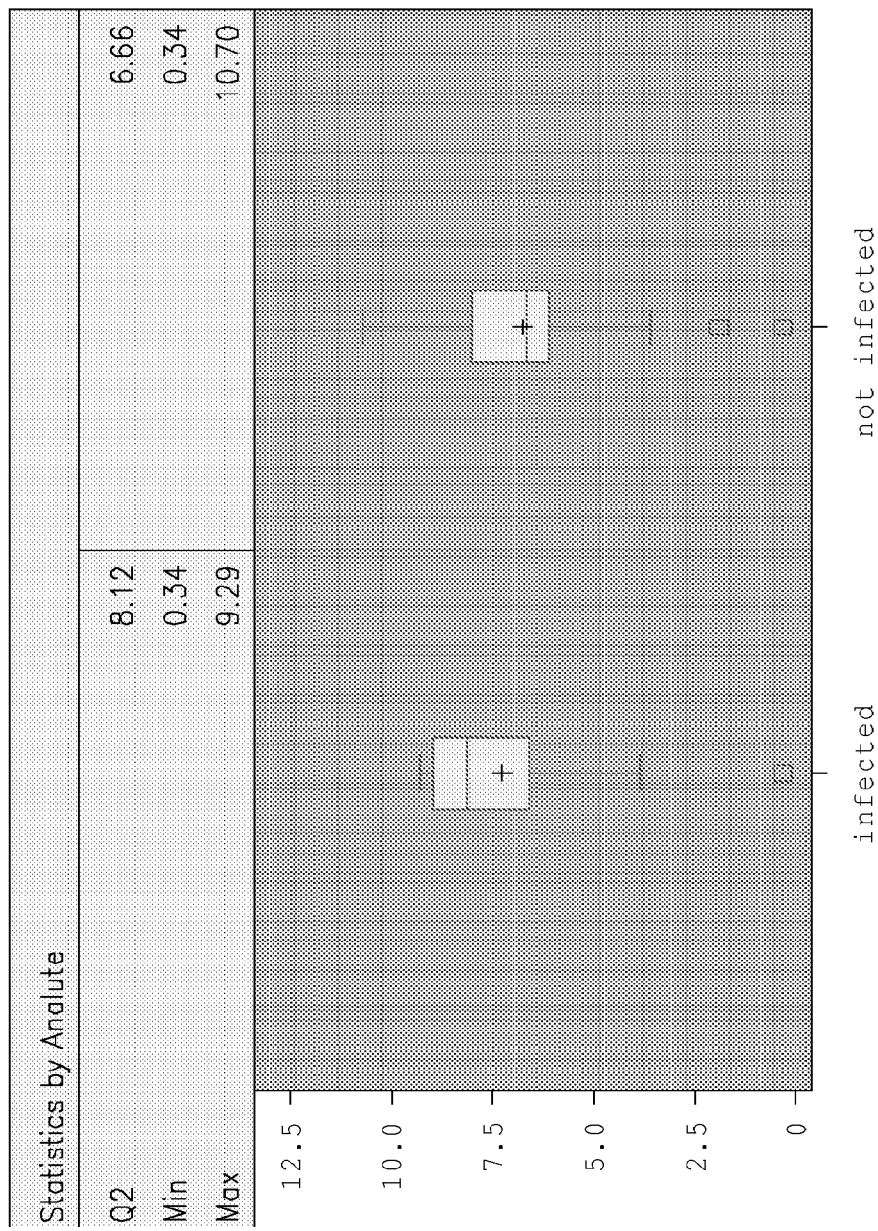
FIG. 6 depicts boxplots showing natural logarithm value of A1AG in IAI infected (n=14) vs. non-infected patients (n=95).

Any residual liquid was removed as before. 100 µL of 1-STEP™ Ultra TMB ELISA (Thermo Scientific, Catalog Number 34028) was added to each well. The wells were covered with aluminum foil and incubated at RT for 2.75 min. 100 µL of Stop Reagent for TMB Substrate (Sigma, Catalog Number S5814-100 mL) was added to each well. The plate was read at 450 nm using the BioTek SYNERGY™ 2 plate reader and the BioTek GEN5™ software. FIG. 6 depicts boxplots showing natural logarithm value of A1AG in IAI infected (n=14) vs. non-infected patients (n=95).

Quantitation of A1AG in CVF Specimens.

Using the GEN5™ software, four parameter nonlinear regression analysis was performed to generate a standard curve. This standard curve was then used to calculate the concentrations of A1AG in the CVF specimens run on the immunoassay kit. In order to calculate the final concentrations of A1AG in the CVF specimens, the calculated concentrations were multiplied by 200 in order to account for the initial specimen dilution. Any specimens that had OD450 readings lower than the OD450 reading of the 3.90625 ng/mL standard were assigned a concentration of 3.90625 ng/mL, which was then multiplied by 200.

Any specimens that had OD450 readings higher than the OD450 reading of the 250 ng/mL standard were diluted at higher dilutions and run on the kit again. The data were then analyzed using statistical methods as described below.

Detection and Quantitation of MIP-1Beta, AFP, B2MG, MCP-1, TIMP-1 and VCAM-1 in CVF Specimens.

Figure 2:
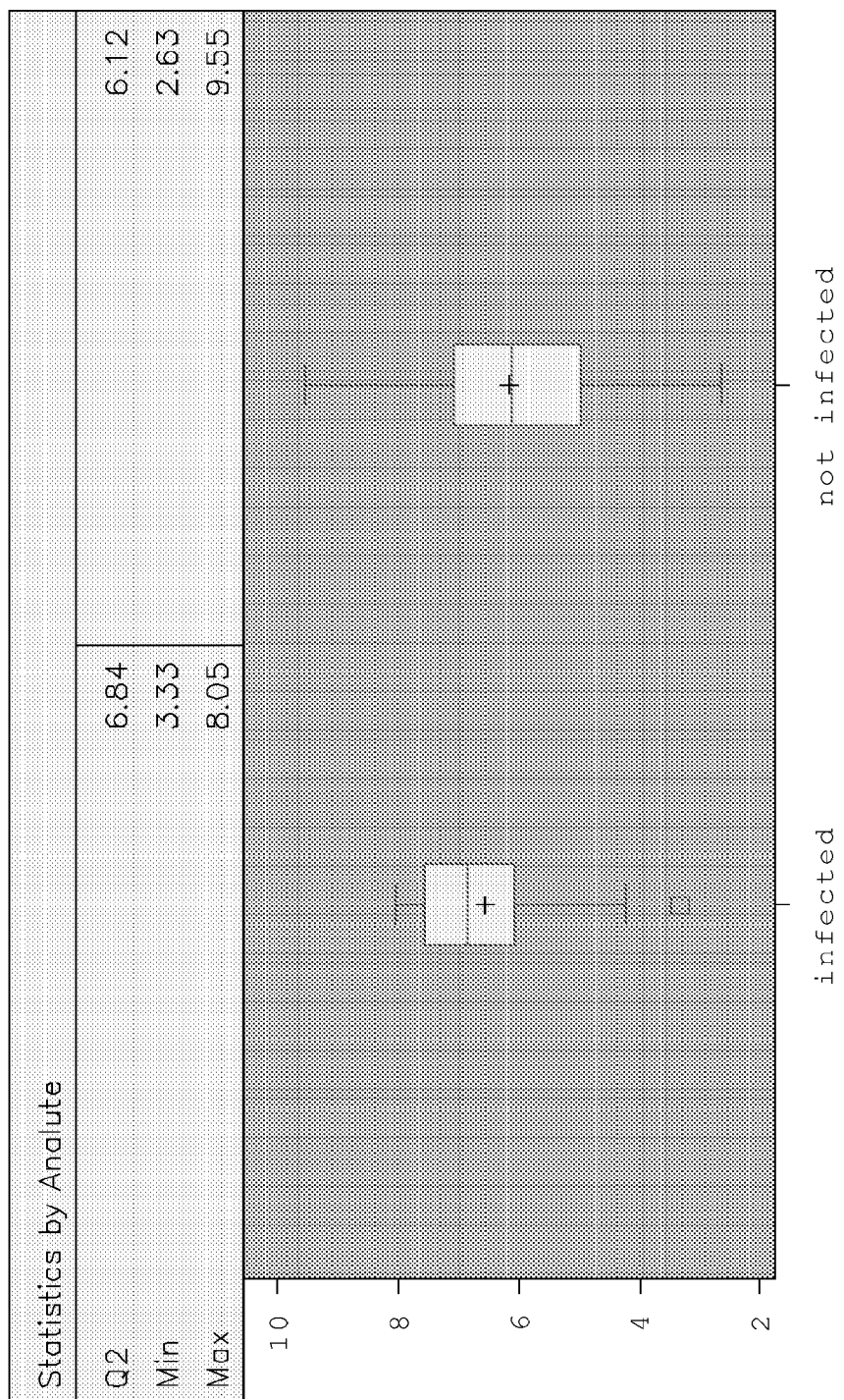
FIG. 2 depicts boxplots showing natural logarithm value of MIP1b in IAI infected (n=14) vs. non-infected patients (n=95).
Figure 3:
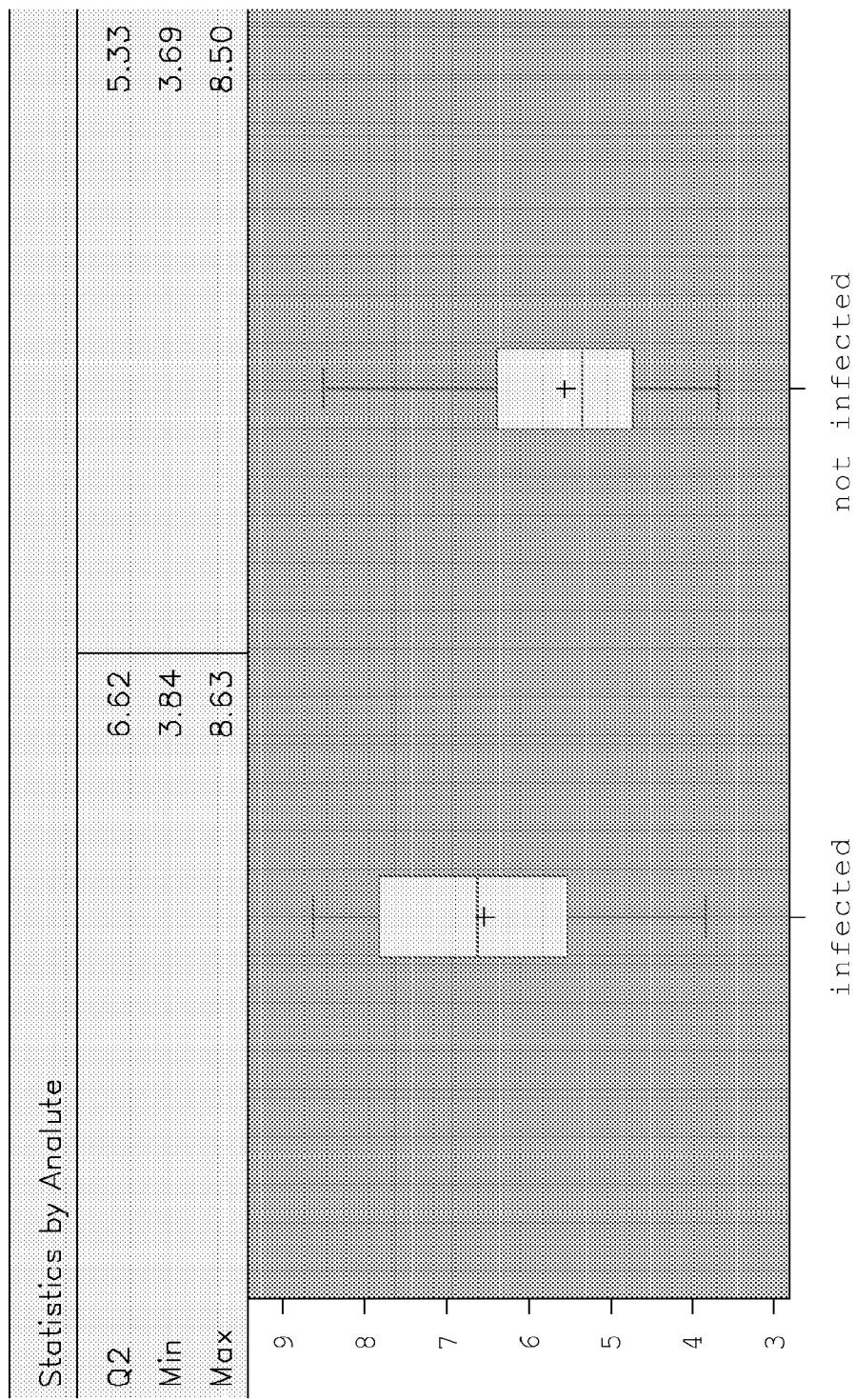
FIG. 3 depicts boxplots showing natural logarithm value of MCP-1 in IAI infected (n=14) vs. non-infected patients (n=95).
Figure 4:
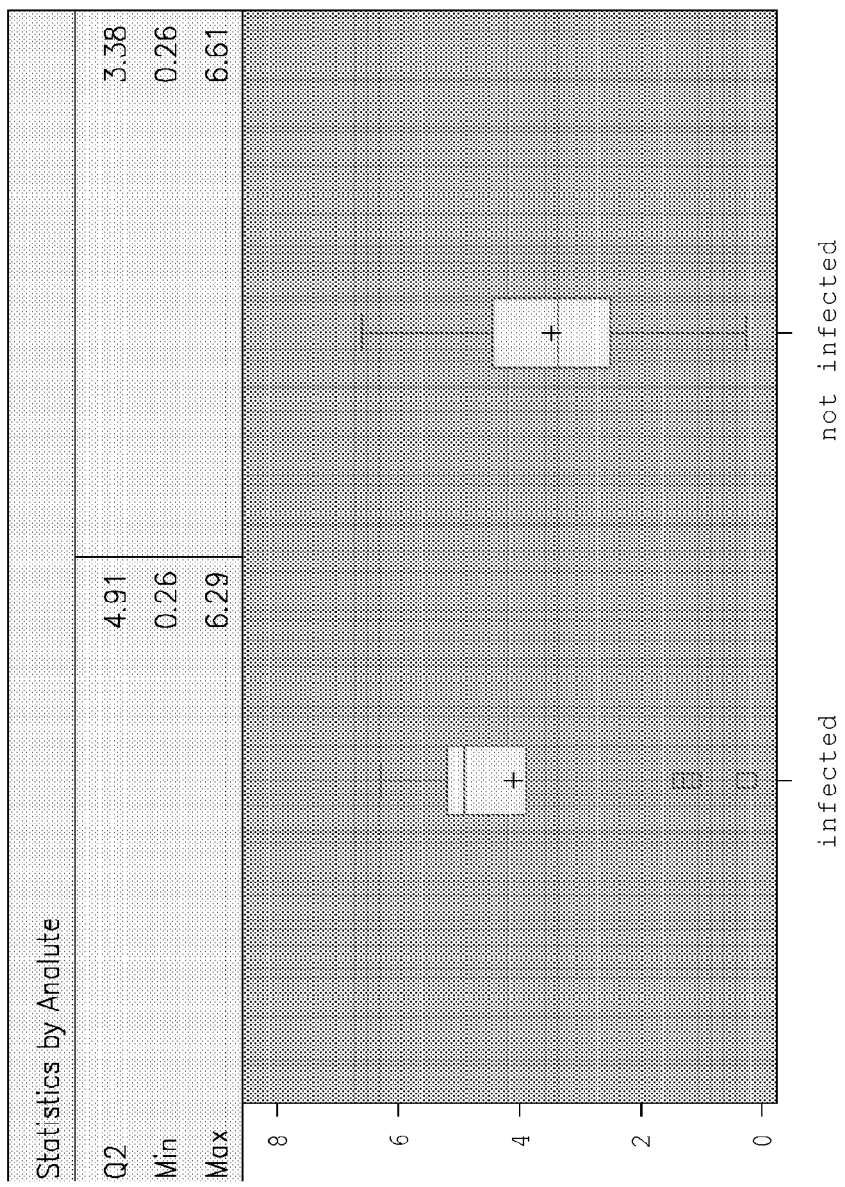
FIG. 4 depicts boxplots showing natural logarithm value of B2MG in IAI infected (n=14) vs. non-infected patients (n=95).
Figure 5:
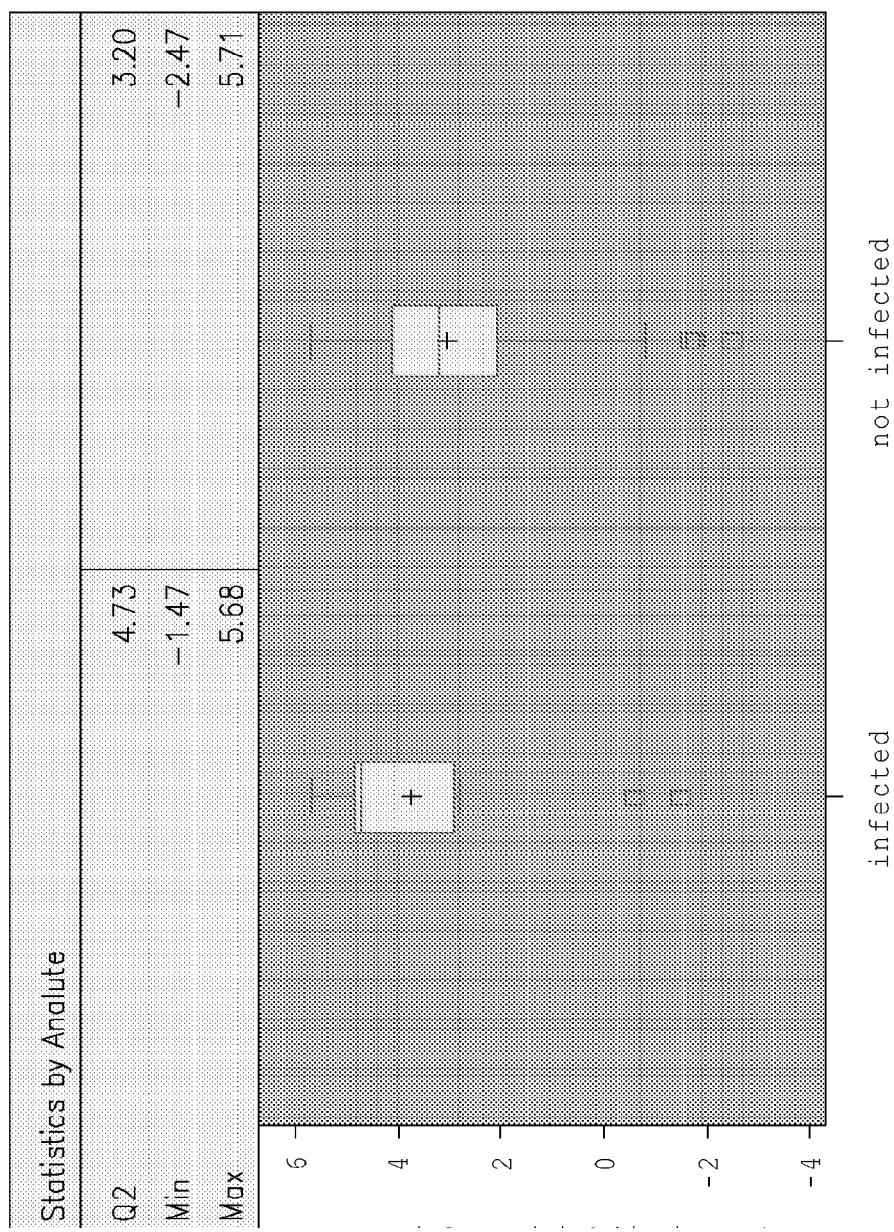
FIG. 5 depicts boxplots showing natural logarithm value of TIMP-1 in IAI infected (n=14) vs. non-infected patients (n=95).
Figure 9:
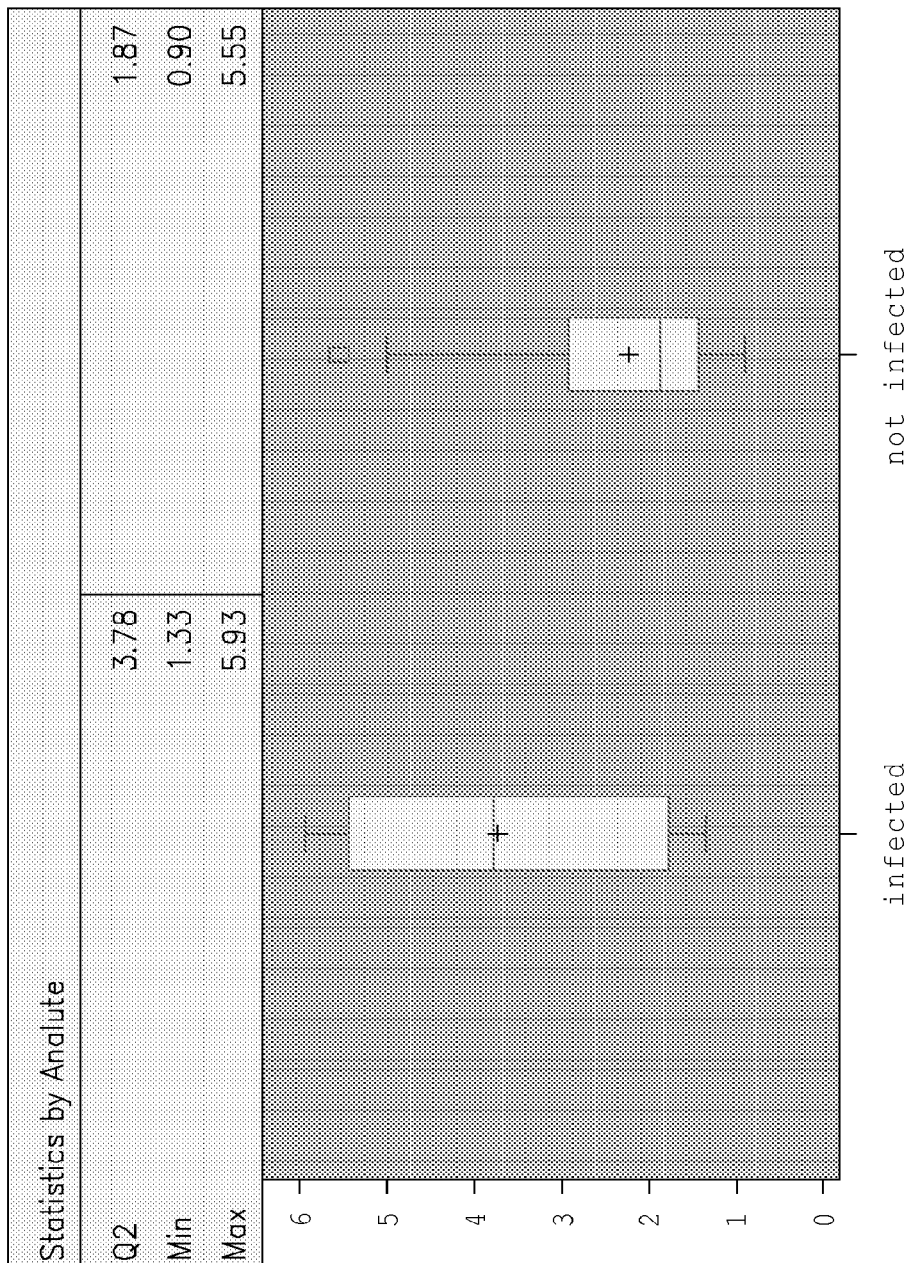
FIG. 9 depicts boxplots showing natural logarithm value of AFP in IAI infected (n=14) vs. non-infected patients (n=95).
Figure 10:
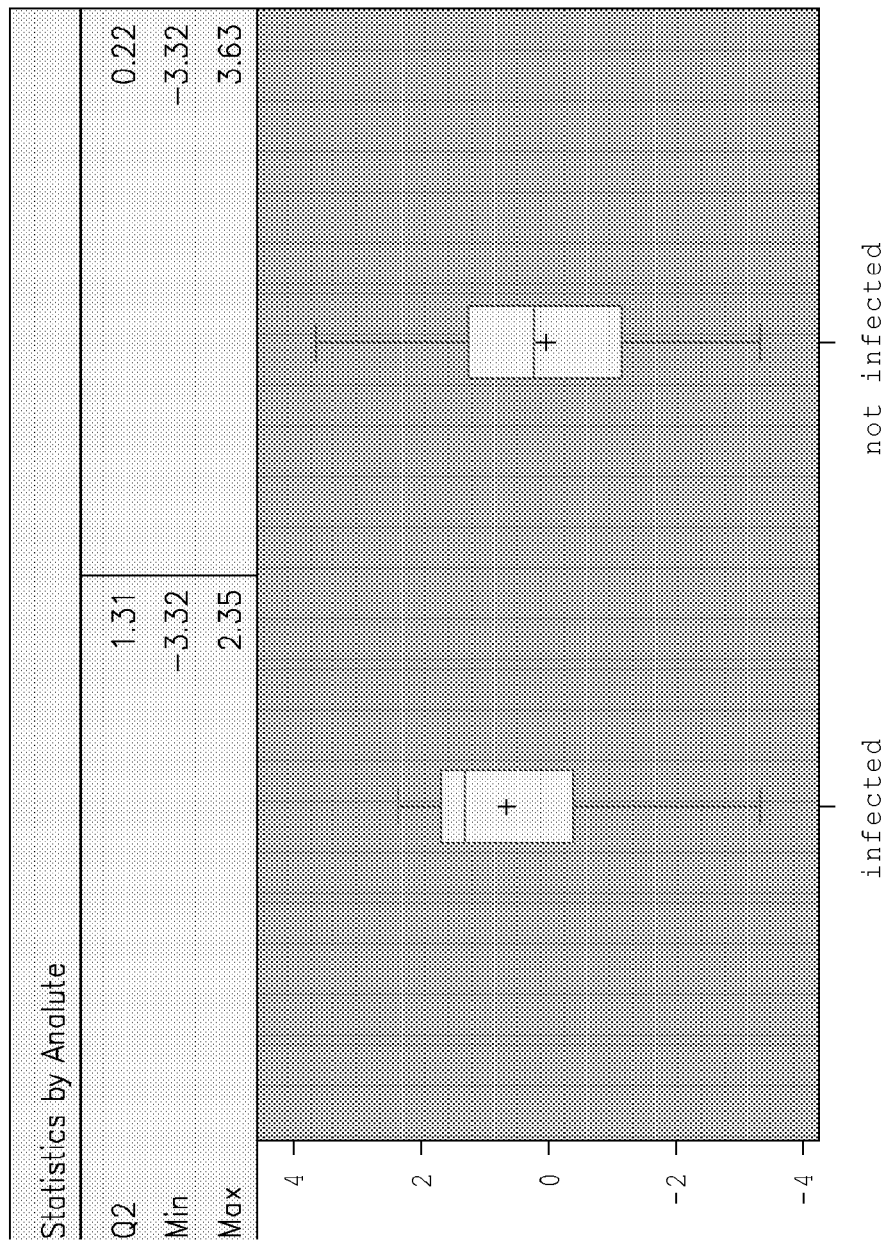
FIG. 10 depicts boxplots showing natural logarithm value of VCAM-1 in IAI infected (n=14) vs. non-infected patients (n=95).

An outside testing laboratory (Rules Based Medicine) was contracted to determine the concentrations of MIP-1beta, AFP, B2MG, MCP-1, TIMP-1 and VCAM-1 in CVF specimens using a multiplexed immunoassay technology (Luminex xMAP®). The data provided by the testing laboratory were then analyzed using statistical methods as described below. FIG. 2 depicts boxplots showing natural logarithm value of MIP1b in IAI infected (n=14) vs. non-infected patients (n=95). FIG. 3 depicts boxplots showing natural logarithm value of MCP-1 in IAI infected (n=14) vs. non-infected patients (n=95). FIG. 4 depicts boxplots showing natural logarithm value of B2MG in IAI infected (n=14) vs. non-infected patients (n=95). FIG. 5 depicts boxplots showing natural logarithm value of TIMP-1 in IAI infected (n=14) vs. non-infected patients (n=95). Boxplots showing natural logarithm value of AFP in IAI infected (n=14) vs. non-infected patients (n=95) are depicted in FIG. 9. Boxplots showing natural logarithm value of VCAM-1 in IAI infected (n=14) vs. non-infected patients (n=95) are depicted in FIG. 10.

Statistical Analyses of Data.

Individual biomarker comparisons were performed as follows: Subjects with infection vs. non-infected status determined via composite reference definition were grouped. A one-way ANOVA to compare groups using natural log-transformed data to reduce influence of outliers was performed. Next, a Wilcoxin rank-based test was performed to compare groups. Finally, receiver-operator characteristic (ROC) curves were generated to assess discriminative ability.

Biomarkers were combined into models using logistic regression. Markers with p<0.20 on Wilcoxin test were considered in multi-marker models. Model-based ROC curves were created and used to compare performance for individual markers to multi-marker models. The intent was to maximize area under the ROC curve and ensure curves met minimally acceptable criteria of 80% sensitivity and specificity. Risk scores were computed based on promising models. Thresholds in risk scores were chosen that maximized sensitivity/specificity of the multi-marker model.

Figure 11:
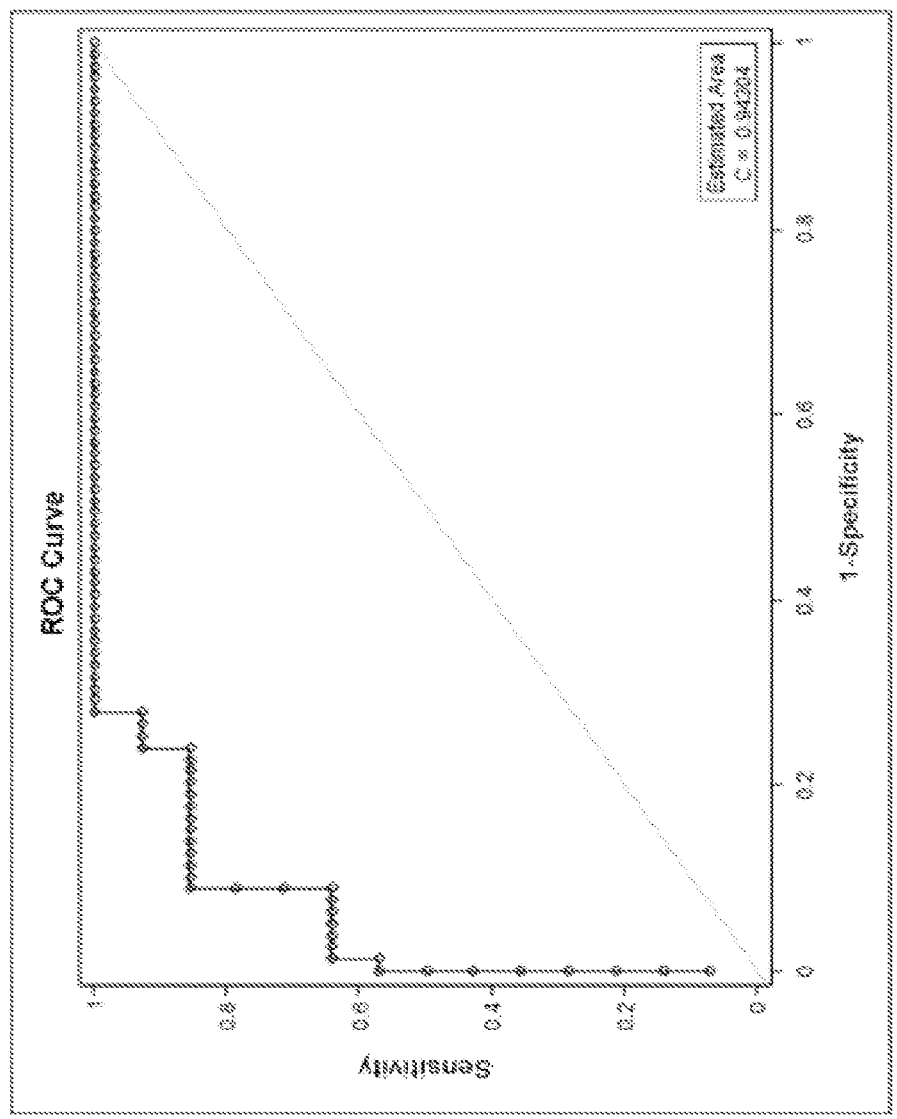
FIG. 11 depicts AUROC of three-marker model for prediction of IAI vs. non-IAI. Sensitivity is 86%, specificity is 85%.
Figure 12:
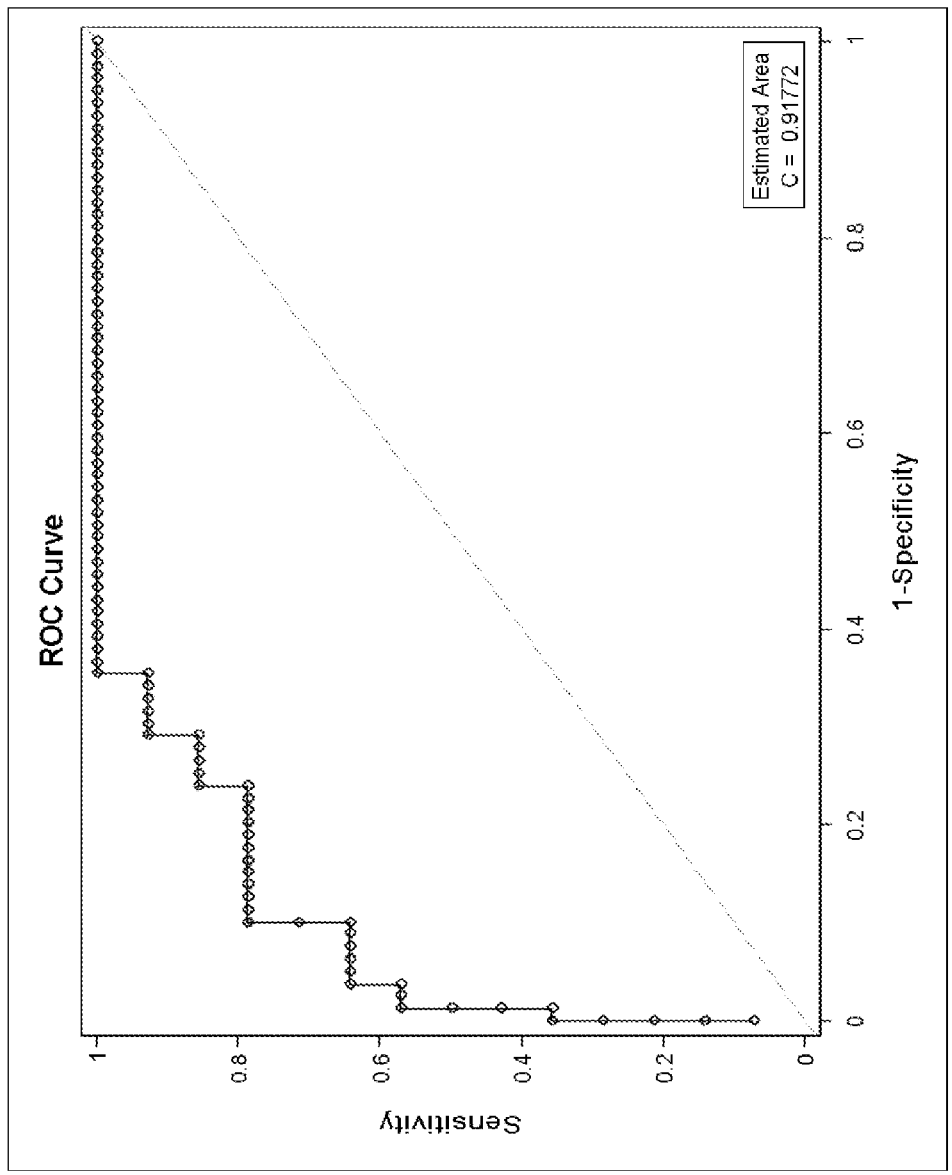
FIG. 12 depicts AUROC of five-marker model for prediction of IAI vs. non-IAI. Sensitivity is x % and specificity is y %.

Area under the individual receiver-operator characteristic curves for ten biomarkers are shown in Table 2 (column labeled "AUROC"). These markers were used in combination with other biomarkers to build logistic regression models for the discrimination of IAI vs. non-IAI, shown in FIGS. 11 and 12. Parameters for each marker in the model are shown below in Table 3. Different combinations of biomarkers performed in multi-marker models in a way superior to individual model performance.

TABLE 2

AUROC and p-values for individual biomarkers associated with prediction of intraamniotic infection.

|  | AUROC | p-value |
|---|---|---|
| AFTP | 0.829 | 0.0001 |
| IL6 | 0.813 | 0.0000 |
| LBP | 0.692 | 0.0146 |
| MCP1 | 0.686 | 0.0270 |

TABLE 2-continued

AUROC and p-values for individual biomarkers associated with prediction of intraamniotic infection.

|        | AUROC | p-value |
|--------|-------|---------|
| B2MG   | 0.632 | 0.1148  |
| A1AG   | 0.617 | 0.2162  |
| TIMP-1 | 0.615 | 0.1588  |
| GRO-ct | 0.607 | 0.1959  |
| MIP1b  | 0.569 | 0.4142  |
| VCAM-1 | 0.598 | 0.2432  |

TABLE 3

Analysis of Maximum Likelihood Estimates.

| Parameter | DF | Estimate | Standard Error | Wald Chi-square | Pr > Chi Sq |
|-----------|----|----------|----------------|-----------------|-------------|
| Intercept | 1  | 7.1935   | 7.5066         | 0.9183          | 0.3379      |
| AFTP      | 1  | 0.6788   | 0.3701         | 3.3641          | 0.0666      |
| IL6       | 1  | 1.3192   | 0.5689         | 5.3769          | 0.0204      |
| LBP       | 1  | 0.1894   | 0.7334         | 0.0667          | 0.7962      |
| A1AG      | 1  | −0.3369  | 0.2833         | 1.4139          | 0.2344      |
| Groa      | 1  | −2.3908  | 1.1906         | 4.0321          | 0.0446      |

Example 2

Development set data for CVF biomarkers was analyzed to assess whether a cutoff for individual biomarker concentrations could be used to classify patients as having a risk for intraamniotic infection. Individual CVF biomarker concentrations are expressed as mass units directly or normalized values of these mass units. Quantitative values were analyzed for individual biomarkers and for combinations of biomarkers. The cutoff approach allows the CVF IAI test to be formatted as a lateral flow device. In a lateral flow format, biomarker levels are quantitatively scored by measuring band intensity on a lateral flow reader.

A combination of single-analyte ELISAs and multiplexed liquid bead arrays based on the xMAP™ technology was used to identify biomarkers of IAI. A cohort of human cervical vaginal fluid specimens (N=112) having an TAT prevalence of 15% was collected in the ProteoGenix IAI Specimen Banking Trial. Amniotic fluid from these subjects was tested by aerobic, anaerobic and *Mycoplasma* culture as well as with an in-house 16S rDNA PCR tests in order to establish the intraamniotic infection status. ELISA and xMAP™ immunoassay data on CVF were analyzed using logistic regression analysis, as well as principle component analysis, to select the top eight CVF biomarkers capable of discriminating IAI from non-IAI patients. From these eight biomarkers, the final three was selected in accordance with the present invention.

Data from ELISA studies were used to simulate lateral flow readings. Cutoffs were chosen to maximize sensitivity since the intent is to use the CVF IAI test as an aid to assess the risk for IAI. Other commonly available tests, such as amniotic fluid glucose, Gram stain or culture could be used to confirm the diagnosis of IAI. The cutoff approach allows the results of the PG-IAI test to be reported as a binary result such as high or low risk for infection.

The best model to date uses the mass concentrations of only two biomarkers, α-fetoprotein and IL-6. Patient specimens with no detectable albumin (6/298) or grossly hemolyzed (11/292) were removed from the data set. Based on the composite reference standard of culture or 16S rDNA, there were 23 infected and 258 non-infected in this data set.

Figure 13:
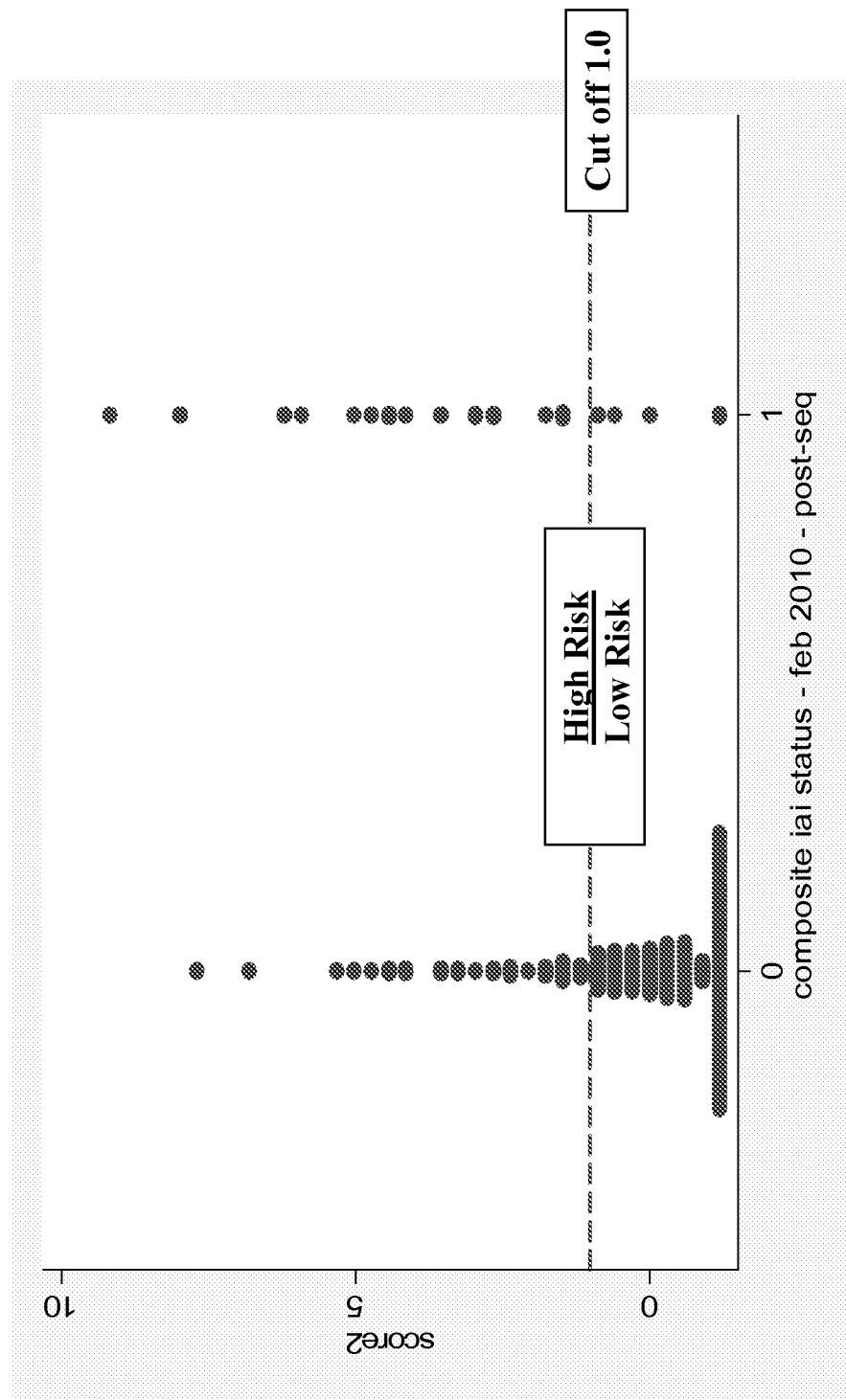
FIG. 13 depicts biomarker Z score levels for composite IAI status of 0 or 1.
Figure 14:
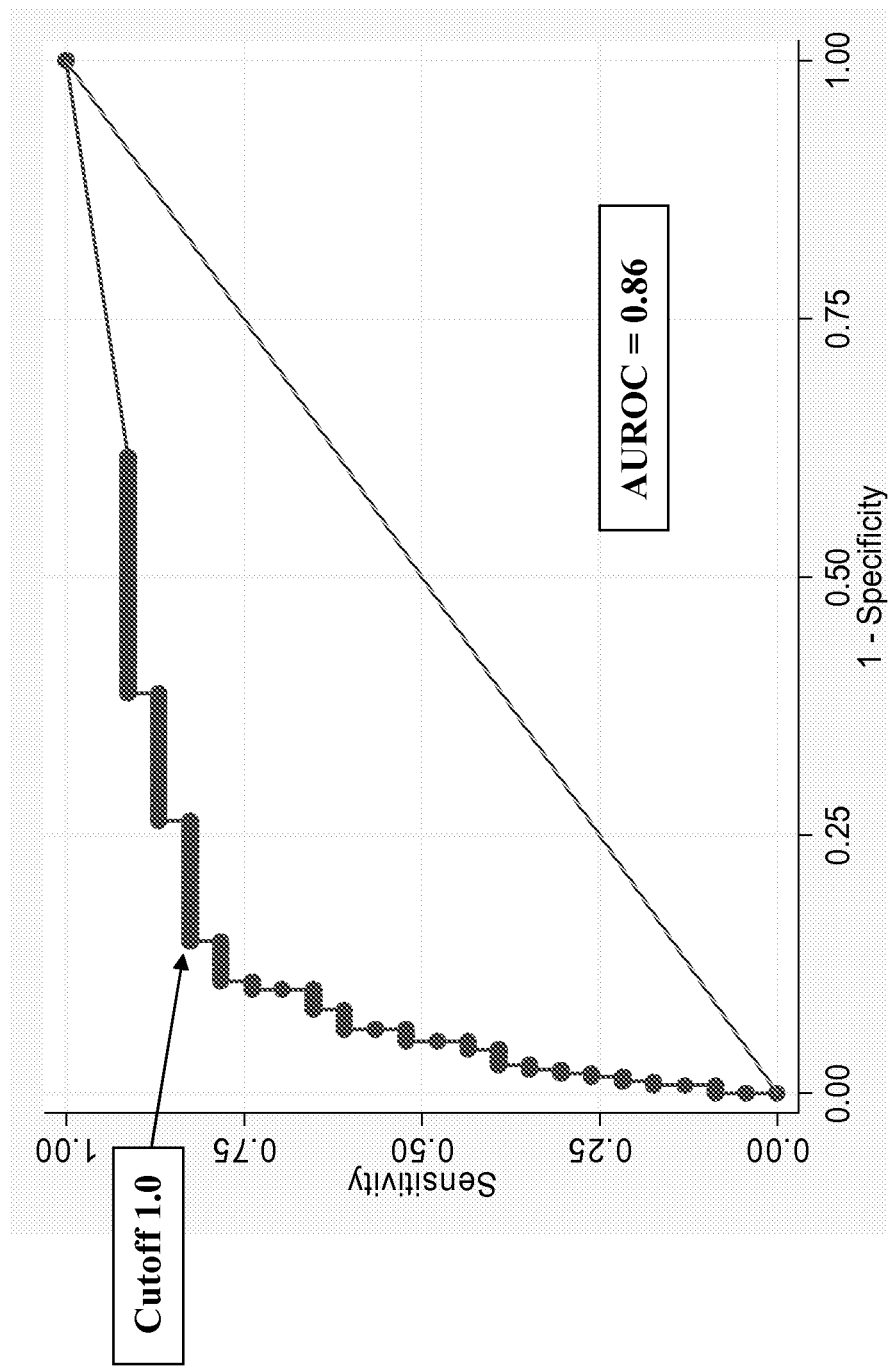
FIG. 14 depicts the data shown in FIG. 13 plotted as Sensitivity versus 1-Specificity, with an AUROC of 0.86. The sensitivity was 82%, specificity 85%, PPV 33%, and NPV 98%.

The results are shown in FIGS. 13 and 14. Biomarker concentrations were log transformed and the Z score calculated. A Z score sum cutoff of 1.0 was used in this ELISA data set. The sum of the Z score of the two biomarkers was determined, ranked and a cutoff determined. The sensitivity was 82%, specificity 85%, PPV 33% and NPV 98%. The AUROC was 0.86.

An additional CVF biomarker, Insulin Growth Factor Binding Protein-1 (IGFBP-1) has been identified, which serves as a gatekeeper to the two biomarker risk factor panel. The IGFBP-1 biomarker is not diagnostic for IAI but rather excludes a number of IAI false positive results (based on the composite reference standard) and significantly improves specificity of the PG-IAI risk factor test.

Figure 15:
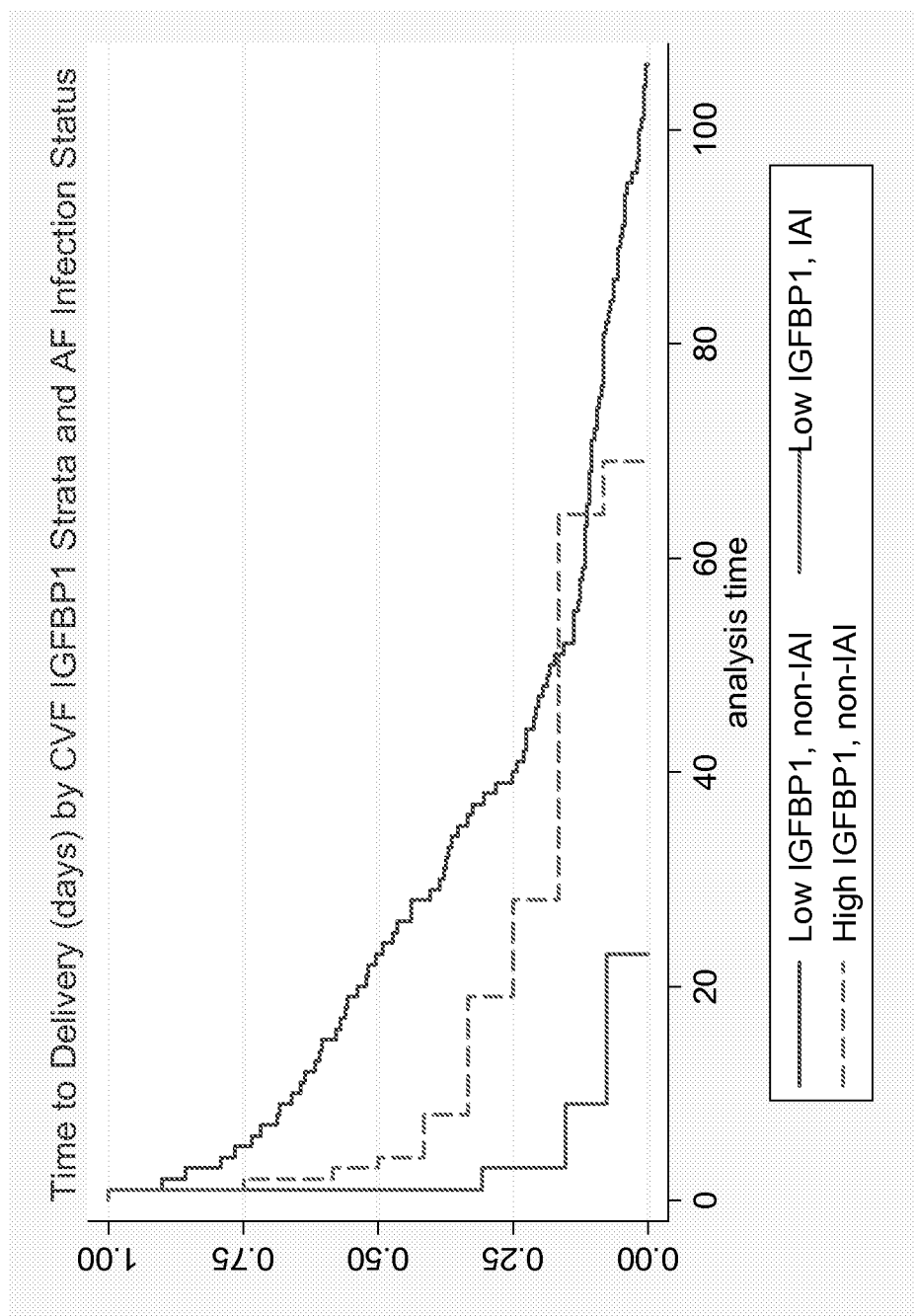
FIG. 15 depicts a Kaplan-Meier graph showing time-to-delivery by CVF status and AF infection status.

IGFBP-1 has been used as a biomarker in cervical vaginal fluid to detect rupture of the fetal membrane (AMNISURE® Test; Medix Biochemica ACTIM PROM™ Test). The concentration of IGFBP-1 is 1000 to 10.000-fold greater in amniotic fluid than cervical vaginal fluid. In the ProteoGenix cohort, the absence of premature rupture of the membrane (PROM) was verified by negative Fern, nitrazine, pooling and/or AMNISURE® tests. As shown in the Kaplan-Meier graph below, concentrations of CVF IGFBP1 greater than 3 μg/mL are consistent with non-IAI preterm birth. The results are shown in FIG. 15.

Figure 16:
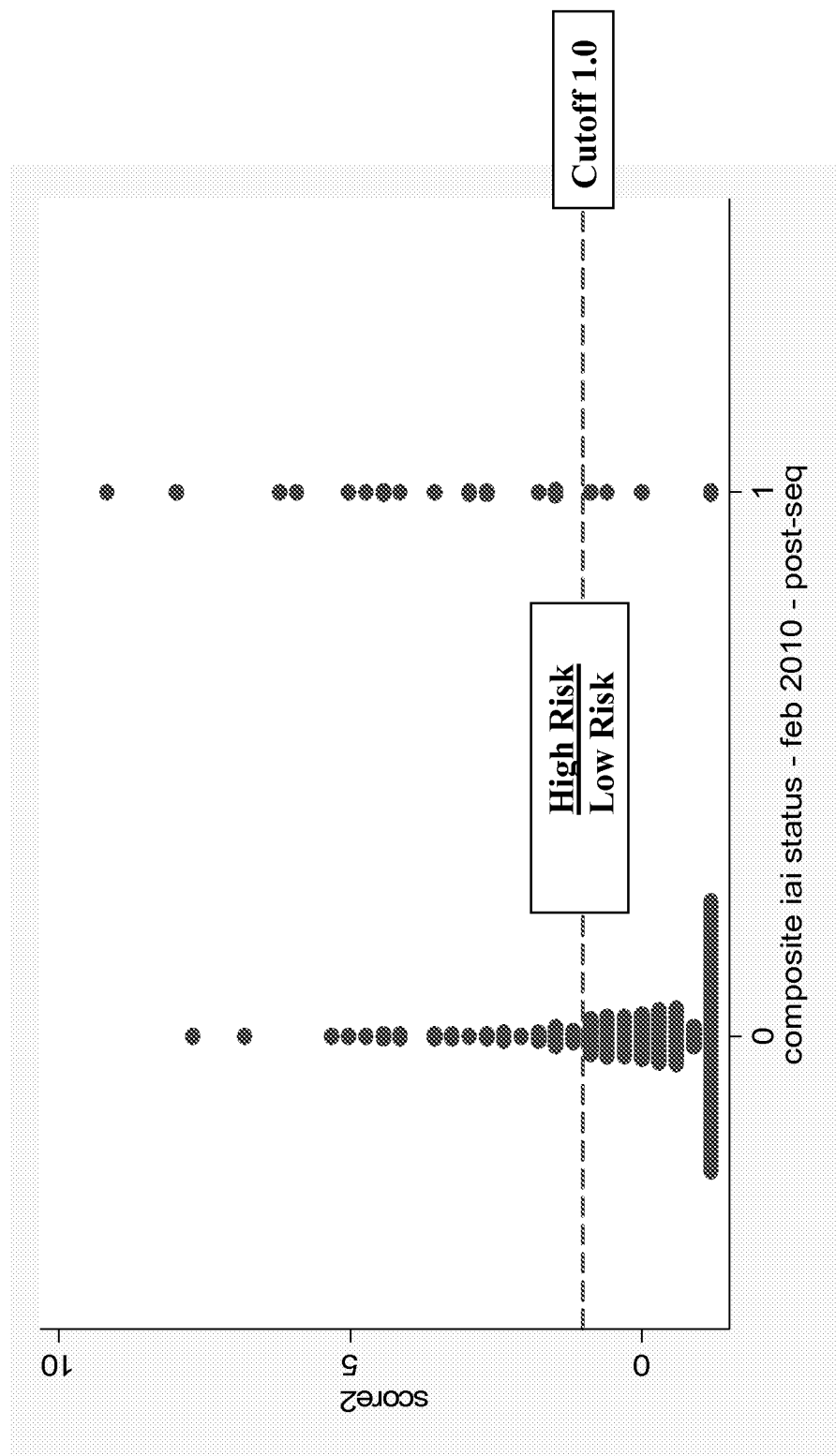
FIG. 16 depicts biomarker Z score levels for composite IAI status of 0 or 1.
Figure 17:
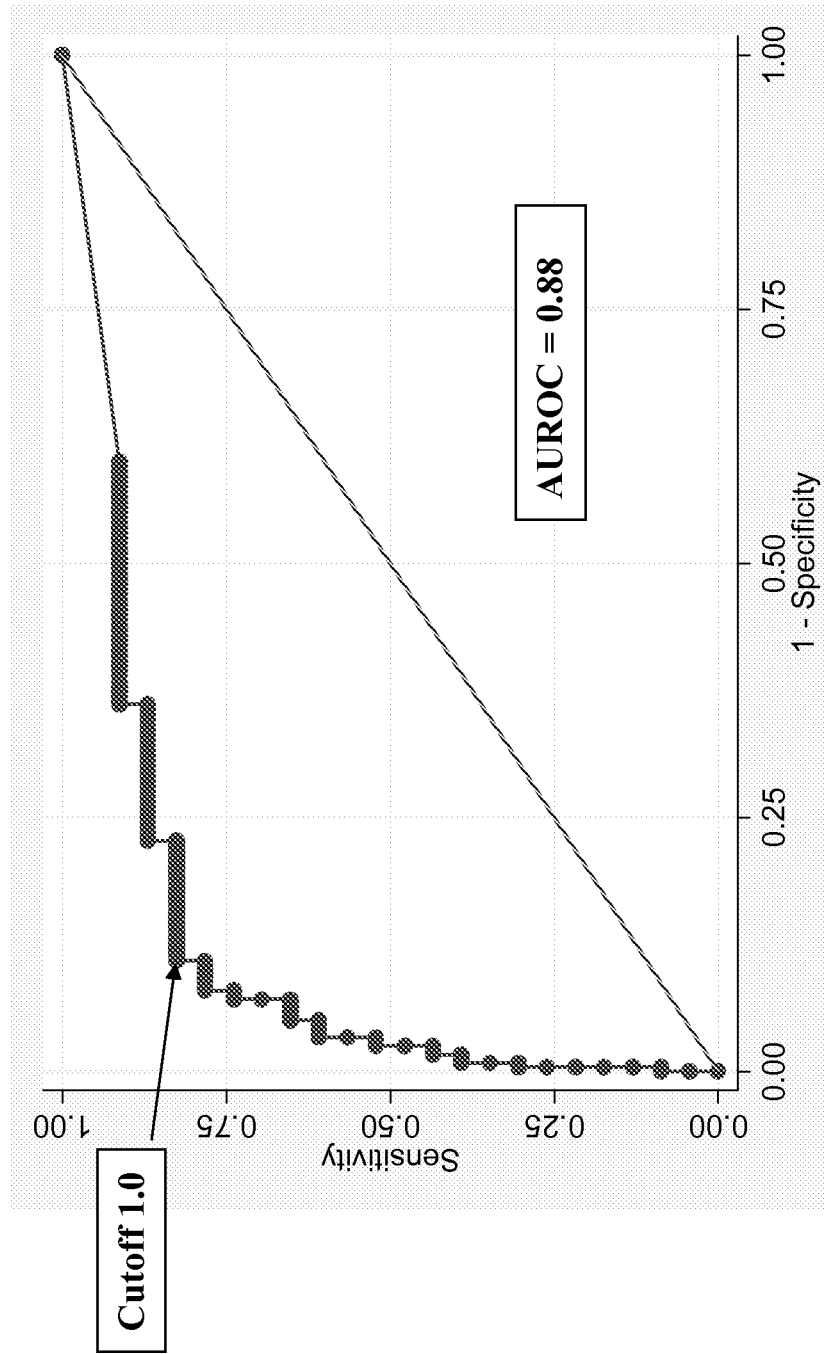
FIG. 17 depicts the data shown in FIG. 16 plotted as Sensitivity versus 1-Specificity, with an AUROC of 0.88. The sensitivity was 82%, specificity 89%, PPV 41%, and NPV 98%.

Patient specimens with no detectable albumin (6/298), grossly hemolyzed (11/292) or IGFBP1 concentrations greater than 3 μg/mL (15/281) were removed from the data set. Based on the composite reference standard of culture and/or 16S rDNA, there were 23 infected and 243 non-infected in this data set. The two diagnostic biomarker concentrations were log transformed and the Z score calculated. A Z score sum cutoff of 1.0 was used. The sum of the Z score of the two biomarkers was determined, ranked and a cutoff determined. The sensitivity was 82%, specificity 89%, PPV 41% and NPV 98%. The AUROC improved from 0.86 to 0.89. 11 of 38 (29%) false positive patient specimens were eliminated resulting in an improvement of specificity from 85% to 89% and PPV from 33% to 41%. In the N=266 patient cohort, 17% have a high risk score. The results are shown in FIGS. 16 and 17.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method for the diagnosis of intra-amniotic inflammation or infection in a pregnant female mammalian subject comprising:
   (a) measuring in a sample of cervical-vaginal fluid obtained from said subject the levels of interleukin-6 (IL-6) and fetal fibronectin (fFN) relative to the corresponding levels of said proteins in normal cervical-vaginal fluid or cervical-vaginal fluid known to be indicative of intra-amniotic inflammation or infection; and
   (b) diagnosing said subject with intra-amniotic inflammation or infection if each of said levels of each of said proteins in said sample is determined to show a statistically significant difference relative to the corresponding levels of each of said proteins in said normal cervical-vaginal fluid, or is determined not to show a statistically significant difference relative to the corresponding levels of each of said proteins in said cervical-vaginal fluid known to be indicative of intra-amniotic inflammation or infection.

2. The method of claim 1 wherein the subject is a human patient.

3. The method of claim 1 wherein said protein level is determined by methods comprising the use of an immunoassay, a protein array, an immunochromatographic test, mass spectrometry, or combinations thereof.

4. The method of claim 3 wherein said level is determined using an immunochromtaographic test employing a lateral flow device.

5. The method of claim 4, wherein the lateral flow device is an immunochromatographic strip (ICS) test.

6. The method of claim 3 wherein said immunoassay employs antibodies and reagents for the detection of IL-6 and fFN.

7. The method of claim 6, wherein the antibodies and reagents comprise a capture antibody and a detector antibody.

8. The method of claim 7, wherein the capture antibody and detector antibody are monoclonal antibodies.

9. The method of claim 7, wherein the capture antibody and detector antibody are polyclonal antibodies.

10. The method of claim 7, wherein the capture antibody and detector antibody are either monoclonal or polyclonal antibodies.

11. The method of claim 8, wherein the antibodies comprise monoclonal antibodies having binding specificity for IL-6 and fFN, and wherein the method further comprises use of an anti-antibody immunoglobulin.

12. The method of claim 11, wherein the monoclonal antibodies and the anti-antibody immunoglobulin are provided in an amount of about 0.001 mg to about 100 grams.

13. The method of claim 11, wherein the monoclonal antibodies and the anti-antibody immunoglobulin are provided in an amount of about 0.01 mg to about 1 gram.

14. The method of claim 11, wherein the anti-antibody immunoglobulin is selected from the group consisting of a polyclonal immunoglobulin, protein A and protein G, or functional fragments thereof.

15. The method of claim 14, wherein the anti-antibody immunoglobulin is labeled.

16. The method of claim 6, further comprising use of agents for reducing background interference in a test or agents for increasing signal.

17. The method of claim 6, further comprising use of software and algorithms for combining and interpolating marker values to produce a prediction of clinical outcome of interest.

18. The method of claim 6, further comprising use of an apparatus for conducting a test.

19. A method for determining signs and symptoms indicating intra-amniotic inflammation or infection comprising
  (a) measuring in a sample of cervical-vaginal fluid obtained from said subject the levels of interleukin-6 (IL-6) and fetal fibronectin (fFN), relative to the levels of IL-6 and fFN in normal cervical-vaginal fluid or cervical-vaginal fluid known to be indicative of intra-amniotic inflammation or infection; and
  (b) diagnosing said subject with intra-amniotic inflammation or infection if each of said levels of IL-6 and fFN in said sample are determined to show a statistically significant difference relative to the corresponding levels of IL-6 and fFN in said normal cervical-vaginal fluid, or are determined not to show a statistically significant difference relative to the corresponding levels of IL-6 and fFN in said cervical-vaginal fluid known to be indicative of intra-amniotic inflammation or infection.

20. The method of claim 19, wherein the signs and symptoms comprise maternal fever, maternal leukocytosis, maternal and/or fetal tachycardia, uterine tenderness, and/or foul-smelling amniotic fluid.

21. The method of claim 19 wherein said protein level is determined by methods comprising the use of an immunoassay, a protein array, an immunochromatographic test, mass spectrometry, or combinations thereof.

22. The method of claim 20, wherein the maternal fever is $>37.8°$ C.

23. The method of claim 20, wherein the maternal leukocytosis is $>15,000 /mm^3$.

24. The method of claim 19, wherein said protein level is determined by methods comprising the use of an immunoassay, a protein array, an immunochromatographic test, mass spectrometry, or combinations thereof.

* * * * *